United States Patent
Lee et al.

(10) Patent No.: US 10,555,972 B2
(45) Date of Patent: Feb. 11, 2020

(54) THERAPEUTIC EFFECTS OF NURR1 AND FOXA2 IN INFLAMMATORY NEUROLOGIC DISORDERS BY M1-TO-M2 POLARIZATION OF GLIAL CELLS

(71) Applicant: INNOPEUTICS CORPORATION, Seoul (KR)

(72) Inventors: Sang-Hun Lee, Seoul (KR); Sang-Min Oh, Seoul (KR)

(73) Assignee: INNOPEUTICS CORPORATION, Seoul (KR)

( * ) Notice: Subject to any disclaimer, the term of this patent is extended or adjusted under 35 U.S.C. 154(b) by 30 days.

(21) Appl. No.: 15/442,473

(22) Filed: Feb. 24, 2017

(65) Prior Publication Data
US 2017/0354688 A1  Dec. 14, 2017

(30) Foreign Application Priority Data
Feb. 26, 2016  (KR) ........................ 10-2016-0023349

(51) Int. Cl.
| | |
|---|---|
| *A61K 48/00* | (2006.01) |
| *A61K 38/18* | (2006.01) |
| *C07K 14/475* | (2006.01) |
| *A61K 35/30* | (2015.01) |
| *A61K 38/17* | (2006.01) |
| *C07K 14/47* | (2006.01) |
| *C07K 14/705* | (2006.01) |
| *C12N 5/079* | (2010.01) |
| *A61K 38/00* | (2006.01) |

(52) U.S. Cl.
CPC .......... *A61K 35/30* (2013.01); *A61K 38/1709* (2013.01); *A61K 38/1783* (2013.01); *C07K 14/4705* (2013.01); *C07K 14/70567* (2013.01); *C12N 5/0622* (2013.01); *A61K 38/00* (2013.01); *A61K 48/00* (2013.01); *C12N 2502/081* (2013.01); *C12N 2502/086* (2013.01); *C12N 2510/00* (2013.01); *C12N 2740/16043* (2013.01)

(58) Field of Classification Search
None
See application file for complete search history.

(56) References Cited

PUBLICATIONS

Yi et al., Foxa2 acts as a co-activator potentiating expression of the Nurr1-induced DA phenotype via epigenetic regulation Development (2014) 141, 761-772.*
Kittappa et al 2007 The foxa2 Gene Controls the Birth and Spontaneous Degeneration of Dopamine Neurons in Old Age PLoS Biology pp. 2875-2884.*
Varnum et al The Classification of Microglial Activation Phenotypes on Neurodegeneration and Regeneration in Alzheimer's Disease Brain Arch. Immunol. Ther. Exp. (2012) 60:251-266.*
Weinberg et al., Adeno-associated virus (AAV) gene therapy for neurological disease Neuropharmacology 69 (2013) 82e88.*
Gonzalez et al Journal of Neuroimmunology Journal of Neuroimmunology 274 (2014) 1-13.*
Tang et al 2013 American Journal of Respiratory Cell and Molecular Biology pp. 960-970 Foxa2 Regulates Leukotrienes to Inhibit Th2-mediated Pulmonary Inflammation.*
McCown et al Differential and persistent expression patterns of CNS gene transfer by an adeno-associated virus ( AA V) vector Brain Research 713 (1996) 99-107 Research report.*
Blood-brain barrier' From Wikipedia, the free encyclopedia; pp. 1-15, down loaded Jul. 2, 2019.*
Terzi et al Adeno-associated virus-mediated gene delivery approaches for the treatment of CNS disorders Biotechnol. J. 2008, 3, 1555-1563.*
Villarreal et al S100B alters neuronal survival and dendrite extension via RAGE-mediated NF-κb signaling, J Neurochem 117: 321-332.*
Saijo et al., "A Nurr1/CoREST Pathway in Microglia and Astrocytes Protects Dopaminergic Neurons from Inflammation-Induced Death", Cell 137, 47-59, Apr. 3, 2009.
Oh et al., "Combined Nurr1 and Foxa2 roles in the therapy of Parkinson's disease", EMBO Molecular Medicine, vol. 7, No. 5, pp. 510-525, 2015.

* cited by examiner

*Primary Examiner* — Maria G Leavitt
(74) *Attorney, Agent, or Firm* — Knobbe, Martens, Olson & Bear LLP

(57) ABSTRACT

A therapeutic effect of Nurr1 and Foxa2 in inflammatory neurologic disorders by M1-to-M2 polarization of glial cells is provided. Specifically, a method of converting glial cells from an M1 phenotype to an M2 phenotype, wherein Nurr1 and Foxa2 are introduced into the glial cells to be overexpressed in the glial cells and a method of preventing or treating an inflammatory neurologic disorder, which includes glial cells into which Nurr1 and Foxa2 are introduced, or a viral vector loaded with Nurr1 and Foxa2, are provided.

13 Claims, 10 Drawing Sheets

Specification includes a Sequence Listing.

THERAPEUTIC EFFECTS OF NURR1 AND FOXA2 IN INFLAMMATORY NEUROLOGIC DISORDERS BY M1-TO-M2 POLARIZATION OF GLIAL CELLS

CROSS-REFERENCE TO RELATED APPLICATION

This application claims priority to and the benefit of Korean Patent Application No. 2016-0023349, filed Feb. 26, 2016, the disclosure of which is incorporated herein by reference in its entirety.

SEQUENCE STATEMENT

Incorporated by reference herein in its entirety is the Sequence Listing entitled "Sequence_list_ST25," created May 2, 2017, size of 7 kilobytes.

BACKGROUND

1. Field of the Invention

The present invention relates to a method of converting glial cells from an M1 phenotype to an M2 phenotype, in which Nurr1 and Foxa2 are overexpressed when the Nurr1 and Foxa2 are introduced into the glial cells, and a composition for preventing or treating inflammatory neurologic disorders, which includes glial cells engineered with Nurr1 and Foxa2 or viral vectors expressing Nurr1 and Foxa2 or molecules secreted from Nurr1+Foxa2-expressing glial cells.

2. Discussion of Related Art

Most of neurologic disorders including neurodegenerative disorders are basically caused by inflammation or accompanied with chronic inflammation.

These target disorders include neurologic disorders having neuro-inflammation as an etiological cause, for example, neuropathic pain, complex region pain syndrome (CRPS), and the like in addition to cerebral degenerative disorders including Alzheimer's disease, Parkinson's disease, multiple systemic atrophy, amyotrophic lateral sclerosis (ALS), cerebral infarction, vertebral damage, etc.

Nuclear receptor-related factor 1 (Nurr1; also known as NR4A2) is an orphan nuclear receptor initially characterized as a transcription factor which is important for development of midbrain dopamine (mDA) neurons, including the generation, maturation, and axonal pathfinding of mDA neurons. Nurr1 continues to be expressed in adult mDA neurons, and the adult-onset deletion of the corresponding protein results in progressive loss of mDA neurons. In heterozygous Nurr1 mice, mDA neurons are more vulnerable to dopaminergic (DA) neurotoxins. A level of Nurr1 in the mDA neurons decreases in the elderly and Parkinson's disease patients, and polymorphisms and mutations resulting in reduced expression of Nurr1 are associated with familial and sporadic Parkinson's disease. These findings support that Nurr1 exerts a protective effect on adult mDA neurons in a cell-autonomous manner Indeed, several intrinsic mechanisms associated with Nurr1-mediated cell survival have been identified. In addition to the intrinsic role of Nurr1 in the mDA neurons, a recent study (Saijo K et al., (2009) A Nurr1/CoREST pathway in microglia and astrocytes protects dopaminergic neurons from inflammation-induced death. Cell 137: 47-59) has identified an unexpected effect of Nurr1 which is expressed in glial cells in response to stimuli which trigger inflammation, and this Nurr1 suppresses the production of pro-inflammatory cytokines that cause the death of mDA neurons, but does not suggest a therapeutic effect through induction of Nurr1 expression.

In particular, glial cells in nerve tissues include astrocytes and microglial cells and are accessory cells that aid in promoting the functions and survival of neurons. However, under a pathologic condition, the glial cells are instead activated to set up an environment in which the glial cells cause damage to neurons (M1 activation). Meanwhile, it is known that glial cells with an M1 phenotype which set up a diseased environment can be converted into glial cells with an M2 phenotype which promote a therapeutic environment in which the survival and regeneration of neurons is set up.

Therefore, the present inventors have found that various neurologic disorders based on inflammation may be treated since transcription factors Nurr1 and Foxa2 interact with each other to convert glial cells from an M1 phenotype to an M2 phenotype which sets up a therapeutic environment, when the transcription factors are overexpressed in the glial cells. In particular, the present inventors have confirmed that Nurr1 has no or low effects when expressed alone but has an effect of synthesizing and secreting potent anti-inflammatory and neurotrophic factors when expressed in combination with a co-activator Foxa2. Therefore, the present invention has been completed based on these facts.

SUMMARY OF THE INVENTION

Therefore, the present invention is directed to providing a method of converting glial cells from an M1 phenotype to an M2 phenotype, in which Nurr1 and Foxa2 are overexpressed when the Nurr1 and Foxa2 are introduced into the glial cells.

Also, the present invention is directed to providing a composition for preventing or treating an inflammatory neurologic disorder, which includes glial cells engineered with Nurr1 and Foxa2 or a viral vector loaded with Nurr1 and Foxa2 or factors secreted from Nurr1+Foxa2-expressing glial cells.

Also, the present invention is directed to providing a method of preventing or treating an inflammatory neurologic disorder, which includes glial cells engineered with Nurr1 and Foxa2 or a viral vector loaded with Nurr1 and Foxa2 or factors secreted from Nurr1+Foxa2-expressing glial cells.

One aspect of the present invention provides a method of converting glial cells from an M1 phenotype to an M2 phenotype in which Nurr1 and Foxa2 are overexpressed when the Nurr1 and Foxa2 are introduced into the glial cells.

When the Nurr1 and Foxa2 are introduced into the glial cells, the introduction may be carried out using a viral vector, preferably an adeno-associated viral (AAV) vector or a lentiviral vector or RNA replicon vector.

Meanwhile, the Foxa2 may reduce inflammatory factors and increase neurotrophic factors when the Foxa2 is expressed with Nurr1 as a transcription factor.

Another aspect of the present invention provides a composition for preventing or treating an inflammatory neurologic disorder, which includes, as an active ingredient, glial cells engineered with Nurr1 and Foxa2 or a viral vector loaded with Nurr1 and Foxa2 or factors secreted from Nurr1+Foxa2-expressing glial cells.

Another aspect of the present invention provides a method of preventing or treating an inflammatory neurologic disorder, which includes, as an active ingredient, glial cells engineered with Nurr1 and Foxa2 or a viral vector loaded with Nurr1 and Foxa2 or factors secreted from Nurr1+Foxa2-expressing glial cells.

In this case, the inflammatory neurologic disorder may include, neuropathic pain, complex region pain syndrome (CRPS), and the like in addition to cerebral degenerative disorders including Alzheimer's disease, Parkinson's disease, multiple systemic atrophy, amyotrophic lateral sclerosis (ALS), cerebral infarction, vertebral damage, etc.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which.

DETAILED DESCRIPTION OF EXEMPLARY EMBODIMENTS

Figure 1:
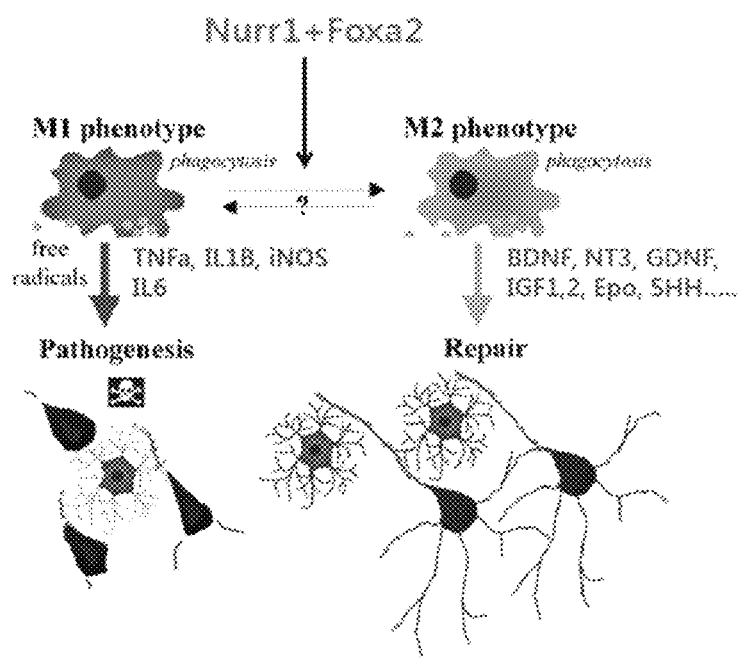
FIG. 1 is a schematic diagram showing a process of converting glial cells from an M1 phenotype to an M2 phenotype, in which Nurr1 and FoxA2 are overexpressed when the Nurr1 and FoxA2 are introduced into the glial cells [an inflammatory factor (indicated by a red letter) and a neurotrophic factor (indicated by a blue letter)].

Hereinafter, exemplary embodiments of the present invention will be described in detail. However, the present invention is not limited to the embodiments disclosed below and can be implemented in various forms. The following embodiments are described in order to enable those of ordinary skill in the art to embody and practice the present invention.

Although the terms first, second, etc. may be used to describe various elements, these elements are not limited by these terms. These terms are only used to distinguish one element from another. For example, a first element could be termed a second element, and, similarly, a second element could be termed a first element, without departing from the scope of exemplary embodiments. The term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The terminology used herein is for the purpose of describing particular embodiments only and is not intended to be limiting the exemplary embodiments. The singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, components and/or groups thereof and do not preclude the presence or addition of one or more other features, integers, steps, operations, elements, components and/or groups thereof.

With reference to the appended drawings, exemplary embodiments of the present invention will be described in detail below. To aid in understanding of the present invention, like numbers refer to like elements throughout the description of the figures, and the description of the same elements will not be iterated.

The terms used in the present invention are defined as follows.

The term "neuron" refers to a cell from the central nervous system, and the terms "neuron" and "neuronal cell" may be interchangeably used herein.

The term "transduction" refers to a process in which a genetic trait is introduced into cells as genetic traits are transferred from one cell to another cell by mean of a bacteriophage. The term "transduction" in biologic researches commonly indicates the process to force a certain exogenous gene expression in target cells using viral vector(s). When any type of bacteria is infected with a bacteriophage, phage DNA binds to host DNA, and bacteriophages holding some of the host DNA rather than some of their own DNA are often released from bacterial cells, when the phages are released through cell lysis. When other bacteria are infected with such phages, a gene of the previous host is introduced into the bacteria so that the bacteria can have a new trait.

In this specification, the term "subject" may refer to a vertebrate to be tested for treatment, observation or experiments, preferably a mammal, for example, a cow, a pig, a horse, a goat, a dog, a cat, a rat, a mouse, a rabbit, a guinea pig, a human, etc.

The term "tissue or cell sample" refers to an assembly of similar cells obtained from tissue of a subject or patient. A source of the tissue or cell sample may be a freshly lyophilized and/or preserved organ or tissue sample or a solid tissue from a biopsy or aspirate; blood or any blood components; or cells at the time of pregnancy or development of the target. The tissue sample may be primary or cultured cells or a cell line.

The term "treatment" refers to an approach used to obtain beneficial or desirable clinical results. For the objects of the present invention, the beneficial or desirable clinical results encompasses palliation of a symptom, a decrease in the extent of a disease, stabilization (that is, no worsening) of a disease condition, a delay of disease progression or a decrease in disease progression rate, (partial or overall) improvement, temporary palliation or a relief of a disease condition, the probability of being either detectable or undetectable, etc., but the present invention is not limited thereto. Also, the "treatment" may refer to an increase in survival rate compared to an expected survival rate when a subject receives no treatment. The "treatment" refers to all types of methods such as therapeutic treatment and prophylactic or preventive measures. The treatments include treatments required for disorders to be prevented and already developed disorders. "Palliating" a disorder refers to reducing an extent of disease condition and/or an undesirable clinical symptom and/or delaying or lengthening a time course of disease progression, compared to the untreated disorders.

The term "cell therapeutic agent" refers to a medicine (U.S. FDA regulations) used for the purpose of treatment, diagnosis and prophylaxis using cells and tissues prepared through isolation from a human, culturing and special homogenization, that is, a medicine used for the purpose of treatment, diagnosis and prophylaxis through a series of actions of proliferating and selecting living autologous, allogenic or xenogenic cells in vitro to restore the functions of cells or tissues, or changing biological characteristics of cells by another method. Cell therapeutic agents are mainly classified into somatic cell therapeutic agents and stem cell therapeutic agents, depending on a differentiation level of the cells.

The term "mammal" in need of treatment refers to any animal classified as a mammal including a human, livestock and farm livestock, and a zoo animal, or pets such as a dog, a horse, a cat, cattle, a monkey, and the like. Preferably, the mammal is a human.

In the present invention, the term "gene therapeutic agent" refers to a medicine in which a genetic material or a delivery system containing the genetic material is administered to a human body for the purpose of treatment of diseases.

In the present invention, the term "administration" means that a composition according to the present invention is introduced to a subject or a patient using any suitable method. In this case, the composition according to the present invention may be administered through various routes of oral or parenteral administration as long as the composition can reach target tissue. The composition may be intraperitoneally, intravenously, intramuscularly, subcutaneously, intradermally, orally, topically, intranasally, intrapulmonarily, and rectally administered, but the present invention is not limited thereto.

In this specification, the term "effective amount" refers to a desired amount required to delay or completely interrupt the onset or progression of a certain disease to be treated. In the present invention, the composition may be administered at a pharmaceutically effective amount. It is apparent to those skilled in the art that a proper amount of the composition used daily is determined by a medical judgment of a general physician.

For the objects of the present invention, a specific therapeutically effective amount for certain subjects or patients is preferably appropriately applied according to various factors including the kinds and extents of reactions to be achieved, a specific composition including other preparations used as necessary, age, weight, general physical condition, sex and diet of a subject (patient), the time and route of administration, the secretion rate of the composition, the duration of treatment, and drugs co-administered or used at the same time as the specific composition, and similar factors well known in the field of medicine.

Unless otherwise defined, all of the technical terms used in the present invention have the same meanings as commonly understood by one of ordinary skill in the art to which the present invention belongs. Also, preferred methods or samples are disclosed in this specification, and similar or equivalent methods or samples are also included in the scope of the present invention. The contents of all publications disclosed as references in this specification are incorporated herein.

Hereinafter, the present invention will be described in detail.

The present invention is directed to providing a method of converting glial cells from an M1 phenotype to an M2 phenotype.

The term "glial cells" refer to cells that occupy the largest part of cells present in the brain and include astrocytes or microglial cells, and the glial cells with the M1 phenotype refer to glial cells that are in an activated state in an environment in which a neuron is damaged under a pathologic condition. Also, the glial cells with the M2 phenotype refer to glial cells that are in a state in which a therapeutic environment is set up in which survival and regeneration of the neuron is promoted.

The astrocytes are cells that are involved in protection of neurons, nutrition supply, and inflammation, and the microglial cells are cells that are in charge of inflammation in the brain.

The method of converting glial cells from an M1 phenotype to an M2 phenotype according to the present invention is characterized by including introducing Nurr1 and FoxA2 into the glial cells to overexpress the Nurr1 and FoxA2.

In the present invention, a Foxa2 gene is used together with a Nurr1 gene to convert the glial cells from an M1 phenotype to an M2 phenotype (see examples). Unlike only a minor reduction of pro-inflammatory factors and no change in trophic factors in glial cells induced by expressing Nurr1 alone, pro-inflammatory factor syntheses are greatly reduced and neurotrophic factor syntheses are dramatically increased in glial cells when Nurr1 and Foxa2 are overexpressed together.

Meanwhile, in the method of the present invention, the expression "introducing (transducing) Nurr1 and FoxA2" means that nucleic acids coding for two genes are introduced into the glial cells. The two genes may be introduced separately or at the same time. To introduce genes coding for Nurr1 and FoxA2 into the glial cells, technical methods of introducing a gene into cells well known in the related art, for example, a DNA-calcium precipitation assay, a method using a liposome, a method using polyamines, an electroporation assay, a method using a retrovirus, a method using an adenovirus, a method using an adeno-associated virus (AAV), etc., may be used herein.

Therefore, the introduction of Nurr1 and FoxA2 according to the present invention encompasses a process of inserting nucleic acids coding for Nurr1 and FoxA2 into individual expression vectors or one expression vector and introducing the expression vector(s) into glial cells according to one exemplary embodiment.

Each of the nucleic acids coding for Nurr1 and FoxA2 may be used without limitation as long as each of the nucleic acids has a base sequence coding for Nurr1 and FoxA2 known in the related art. Also, the nucleic acids may have base sequences coding for functional equivalents of Nurr1 and FoxA2. The functional equivalent refers to a polypeptide having a sequence homology (that is, identity) of at least 70%, preferably 80% or more, more preferably 90% or more to amino acid sequences of Nurr1 and FoxA2. For example, the functional equivalent includes polypeptides having a sequence homology of 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and 100%. The functional equivalent may be generated as a result of addition, substitution or deletion of a part of each of the amino acid sequences. Preferably, the deletion or substitution of amino acids occurs at sites which are not directly associated with physiological activities of the polypeptide according to the present invention.

Also, the nucleic acids coding for Nurr1 and FoxA2 may be prepared using a genetic recombination method known in the related art (Sambrook, Fritsch and Maniatis, 'Molecular Cloning, A laboratory Manual, Cold Spring Harbor laboratory press, 1989; Short Protocols in Molecular Biology, John Wiley and Sons, 1992). For example, there is a PCR amplification method of amplifying nucleic acids from a genome, a chemical synthesis method, or a technique of preparing a cDNA sequence.

The nucleic acids coding for Nurr1 and FoxA2 are operably linked to an expression control sequence so that the nucleic acids can be inserted into an expression vector. The expression 'being operably linked' means that one nucleic acid fragment is linked to another nucleic acid fragment so that the function or expression of the one nucleic acid fragment is affected by the another nucleic acids fragment. Also, the expression control sequence refers to a DNA sequence that regulates the expression of a nucleic acid sequence operably linked thereto in certain host cells. Such a control sequence includes a promoter for initiating transcription, any operator sequence for regulating the transcription, a sequence coding for a proper mRNA ribosome-binding site, and a sequence for regulating the termination of transcription and translation. Also, these sequences may be generally expressed with an expression, 'DNA construct including nucleic acids coding for Nurr1 and FoxA2.'

The term 'expression vector' refers to a plasmid, a viral vector, or other mediators into which nucleic acids coding for structural genes may be inserted and in which the nucleic acids may be expressed in host cells, as known in the related art. Preferably, the 'expression vector' may be a viral vector. The viral vector may include an adenoviral vector, an adeno-associated viral (AAV) vector, a herpesviral vector, an avipoxviral vector, a lentiviral vector, etc., but the present invention is not limited thereto. In particular, a method using lentiviruses or adeno-associated viruses (AAVs) is preferred.

The adeno-associated viral (AAV) vector is constructed by introducing materials which may form a virus into certain cells, and the lentiviral vector is also constructed in a series of steps so that a virus can be produced in a certain cell line. Main advantages of the lentiviral or AAV vector for gene therapy include efficiency and stability.

The expression vector carrying the nucleic acids according to the present invention may be introduced into the glial cells using methods known in the related art, for example, transient transfection, microinjection, transduction, cell fusion, a calcium phosphate precipitation assay, liposome-mediated transfection, DEAE dextran-mediated transfection, polybrene-mediated transfection, an electroporation assay, gene gun, and other known methods used to introduce the nucleic acids into cells, but the present invention is not limited thereto. For example, Nurr1 and FoxA2 are inserted into the lentiviral or AAV vector to construct an expression vector, and packaging cells are then transduced with such a vector. The transduced packaging cells are incubated and then filtered to obtain a lentiviral or AAV solution. Then, neural progenitor cells may be infected with the lentiviral or AAV solution to introduce Nurr1 and FoxA2 genes into the glial cells. Subsequently, after confirming that Nurr1 and FoxA2 are co-expressed using a selective marker included in the lentiviral or AAV vector, the desired glial cells may be obtained.

According to one exemplary embodiment, the glial cells overexpressing the Nurr1 and FoxA2 according to the present invention may be prepared using a preparation method including the following steps:

(a) preparing a recombinant viral vector harboring nucleic acids coding for Nurr1 and FoxA2;

(b) transfecting a virus-producing cell line with the recombinant viral vector to prepare a recombinant virus expressing the Nurr1 and FoxA2; and (c) infecting glial cells with the recombinant virus expressing the Nurr1 and FoxA2.

First, a DNA construct harboring the nucleic acids coding for Nurr1 and FoxA2 is as described above. The DNA construct is operably linked to an expression control sequence, for example, a promoter, and inserted to a viral vector known in the related art to prepare a recombinant viral vector. Thereafter, the recombinant viral vector harboring the nucleic acids coding for Nurr1 and FoxA2 is introduced into a virus-producing cell line to prepare a recombinant virus expressing the Nurr1 and FoxA2. A cell line capable of producing a virus corresponding to the viral vector used may be used as the virus-producing cell line. Then, glial cells are infected with the recombinant lentiviruses or AAVs expressing the Nurr1 and FoxA2. This may be carried out using a method known in the related art.

The glial cells overexpressing the Nurr1 and FoxA2 according to the present invention may be proliferated and incubated according to methods known in the related art.

The glial cells of the present invention are incubated in a culture broth that helps survive or proliferate a desired type of cells. A culture broth nourished with free amino acids instead of a serum is preferably used. The culture broth is preferably supplemented with additives developed to continue to culture the glial cells. For example, the additives include an N2 medium and a B27 additive commercially available from Gibco, bovine serum, etc. During incubation, the medium is preferably replaced with a fresh medium while observing the conditions of the medium and cells. In this case, the glial cells are preferably subcultured when the glial cells continue to proliferate into confluence to form neurospheres. The subculturing may be carried out every approximately 7 to 8 days, depending on the situation.

Meanwhile, when the Nurr1 and Foxa2 are overexpressed in the glial cells, the morbid glial cells with an M1 phenotype that kill neurons by secreting inflammatory factors (i.e., pro-inflammatory cytokines) to induce inflammation may be converted into therapeutic glial cells with an M2 phenotype that secretes neurotrophic factors protecting the neurons instead of reducing the secretion of the inflammatory factors, to treat an inflammatory neurologic disorder [FIG. 1].

Also, according to another aspect of the present invention, there is provided a use of the glial cells into which Nurr1 and FoxA2 are introduced to treat an inflammatory neurologic disorder.

For example, these cells may be therapeutically used by directly introducing the glial cells into which the Nurr1 and FoxA2 are introduced at SN (substantia nigra) positions, depending on the disorders or conditions to be treated. Also, the glial cells may also be administered or transplanted in the form of a composition including a therapeutically effective amount of the glial cells, into which the FoxA2 and Nurr1 are introduced, so that the glial cells can be therapeutically used. Optionally, the present invention also includes a method of treating an inflammatory neurologic disorder.

The inflammatory neurologic disorder refers to at least one disease selected from the group consisting of Alzheimer's disease, Parkinson's disease, multiple systemic atrophy, amyotrophic lateral sclerosis (ALS), cerebral infarction, vertebral damage, neuropathic pain, and complex region pain syndrome (CRPS).

One aspect of the present invention is directed to providing a composition or a cell therapeutic agent for preventing or treating an inflammatory neurologic disorder, which includes, as an active ingredient, the glial cells into which the FoxA2 and Nurr1 are introduced.

The cell therapeutic agent of the present invention serves to replenish (regenerate) or reconstruct (restore) damaged dopaminergic neurons. The "regeneration" refers to a situation in which a formed organ or individual part is replenished when some of the formed organ or individual part is lost, and the "restoration" may also be referred to as "reconstitution" which refers to the renewal of tissue. In this case, the restoration means that tissue or organs are again constructed from the dissociated cells or tissue.

The composition or the cell therapeutic agent of the present invention may be prepared into a proper preparation so that the preparation includes an acceptable carrier according to a mode of administration. The preparation suitable for the mode of administration is known and may typically include a preparation passing through a membrane, thereby promoting the movement.

Also, the composition of the present invention may be used in the form of a general medicinal preparation. The composition may be prepared in the form of a sterile aqueous solution, non-aqueous solvent, a suspending agent, an emulsifying agent or a lyophilized preparation for paranteral preparations, and prepared in the form of a tablet, a troche, a capsule, an elixir, a suspension, syrup or a wafer, etc. upon oral administration. An injection preparation may be prepared in the form of a unit dosage ampoule or prepared in multiple dosage forms. Also, the therapeutic composition of the present invention may be administered together with a pharmaceutically acceptable carrier. For example, a binder, a lubricant, a disintegrating agent, an excipient, a solubilizing agent, a dispersing agent, a stabilizing agent, a suspending agent, a pigment, or a flavoring agent may be used in the case of oral administration, and a buffer, a preservative, a soothing agent, a solubilizing agent, an isotonic agent, a stabilizing agent, and the like may be mixed and used in the case of the injection preparation. For topical administration, a base, an excipient, a lubricating agent, a preservative, and the like may be used.

Also, the method of treating an inflammatory neurologic disorder using the therapeutic composition of the present invention may include administering a predetermined material to a subject through a typical route through which the material is introduced into the subject in a suitable manner. The administration method may include intraperitoneal administration, intravenous administration, intramuscular administration, subcutaneous administration, intradermal administration, oral administration, topical administration, intranasal administration, intrapulmonary administration, and rectal administration, but the present invention is not limited thereto. However, since cells may be digested upon oral administration, an oral composition is preferably formulated with a coating over an active drug or formed into tablets to protect the active drug from being decomposed in the stomach.

Also, a pharmaceutical composition may be administered through any device that can deliver an active material to target cells. Preferred administration modes and preparations include an intravenous injection preparation, a subcutaneous injection preparation, an intradermal injection preparation, an intramuscular injection preparation, or a drop injection preparation. The injection preparation may be prepared using an aqueous solvent such as physiological saline or a Ringer's solution, or a non-aqueous solvent such as vegetable oil, a higher fatty acid ester (e.g., ethyl oleate, etc.), an alcohol (e.g., ethanol, benzyl alcohol, propylene glycol, glycerine, etc.), etc. and may include a pharmaceutical carrier such as a stabilizing agent for preventing a change in quality (e.g., ascorbic acid, sodium bisulfite, sodium pyrosulfite, BHA, tocopherol, EDTA, etc.), an emulsifying agent, a buffer for regulating a pH, a preservative for inhibiting the growth of microorganisms (e.g., phenylmercuric nitrate, thimerosal, benzalconium chloride, phenol, cresol, benzyl alcohol, etc.), etc. Preferably, the method of treating an inflammatory neurologic disorder using the therapeutic composition of the present invention includes administering a pharmaceutically effective amount of the therapeutic composition of the present invention. The pharmaceutically effective amount may be readily determined by those skilled in the art, depending on the factors widely known in the field of medicine, such as the type of disease, age, weight, physical condition, and sex of a patient or a subject, the sensitivity of a patient or a subject to drugs, a route of administration, an administration method, the number of administration, the duration of treatment, drugs used in combination or at the same time, etc.

Also, another aspect of the present invention is directed to providing a method of treating an inflammatory neurologic disorder, which includes directly transplanting a therapeutically effective amount of the above-described composition, which includes the glial cells into which FoxA2 and Nurr1 are introduced, into a site of lesion. Transplantation and cell culture methods that may be used herein may include methods widely known to those skilled in the related art.

The term "therapeutically effective amount" of the cells refers to a suitable amount to remove and relieve a physiological effect of or a subject caused by inflammation. The therapeutically effective amount of the cells used may depend on the or subject's needs, age, physiological condition and health, a predetermined therapeutic effect, the size and area of tissue in need of treatment, the severity of lesion, and a selected delivery route. Also, a low cellular dose of the cells may be administered to one or more sites in a predetermine target tissue in the form of small multiple grafts. The cells of the present invention may be completely isolated before transplantation, for example, to form a suspension of single cells or may be almost completely isolated before transplantation, for example, to form small cell aggregates. The cells may be administered by transplanting or moving the cells to a predetermined tissue site and reconstructing or regenerating a functionally deficient region.

A suitable dose range of the cells to be administered to achieve therapeutic effectiveness may be properly used for or subjects, within the ordinary skill of a person skilled in the art. For example, the dose range of the cells may be in a range of approximately 1,000 to 10,000,000 or may also be out of this range. However, since it is impossible to completely exclude the probability of a cancer cell to develop when a large amount of the cells are administered, the dose range of the cells may be in a range of approximately 2,000,000 to 4,000,000.

However, the dose of the cells may be properly finally determined by a physician's opinion in consideration of the type of formulation, an administration method, age or weight of a patient or a subject, symptoms of a patient or a subject, etc., but the present invention is not limited thereto.

Also, the present invention is directed to providing a composition or a gene therapeutic agent for preventing or treating an inflammatory neurologic disorder, which include a viral vector loaded with Nurr1 and FoxA2.

A proper dose of the composition according to the present invention may vary, depending on factors such as a preparation method, an administration mode, age, weight and sex of a patient or a subject, the severity of symptoms of a disease, a food, the duration of administration, a route of administration, a secretion rate, and the sensitivity to response. Generally, a skilled physician may easily determine and prescribe the dose of the composition effective for desired treatment. In general, the composition according to the present invention includes $1 \times 10^{10}$ to $1 \times 10^{13}$ vg/µl of a viral vector or a viral gene and may be typically injected at a dose of $1 \times 10^{12}$ to $3 \times 10^{12}$ vg/µl of a viral vector or a viral gene once per 1 to 2 days over 1 to 15 days.

The viral vector includes an adenoviral vector, an adeno-associated viral (AAV) vector, a herpesviral vector, an avipoxviral vector, a lentiviral vector, and the like, but the present invention is not limited thereto. In particular, a method using a lentiviral or adeno-associated viral (AAV) vector is preferred.

In the present invention, the composition may be used in the form of a medicinal preparation as described above.

In the present invention, the term "gene therapeutic agent" refers to a medicine in which a genetic material or a delivery system containing the genetic material is administered to a subject body for the purpose of treatment of diseases, etc.

For the composition of the present invention which is applicable as the gene therapeutic agent, a pharmaceutically acceptable carrier is sterile and biocompatible. Therefore, saline, sterile water, a Ringer's solution, buffered saline, an albumin injection solution, a dextrose solution, a maltodextrin solution, glycerol, ethanol, and a combination thereof may be used as the pharmaceutically acceptable carrier. As necessary, other conventional additives such as an antioxidant, a buffer, a bacteriostatic agent, and the like may be added. Also, a diluent, a dispersing agent, a surfactant, a binder, and a lubricating agent may be further added to formulate the composition into an injectable formulation such as an aqueous solution, a suspension, or an emulsion, a pill, a capsule, a granule, or a tablet. Also, target organ-specific antibodies or other ligands may bind to the carrier so that the carrier can act in a target organ-specific manner.

Except for the fact that, instead of using the glial cells expressing Nurr1 and FoxA2, the vector expressing Nurr1 and FoxA2 is directly used for the composition, the above-described contents may be directly or indirectly applied to the composition.

The present invention is also directed to providing a method of preventing or treating an inflammatory neurologic disorder, which includes administering, to a subject, a therapeutically effective amount of the composition including the glial cells to which Nurr1 and Foxa2 are introduced.

According to one exemplary embodiment, the glial cells may be astrocytes or microglial cells.

According to one exemplary embodiment, the inflammatory neurologic disorder may include at least one selected from the group consisting of Alzheimer's disease, Parkinson's disease, multiple systemic atrophy, amyotrophic lateral sclerosis (ALS), cerebral infarction, vertebral damage, neuropathic pain, and complex region pain syndrome (CRPS).

Further, the present invention is directed to providing a method of preventing or treating an inflammatory neurologic disorder, which includes administering, to a subject, a therapeutically effective amount of the composition including the viral vector loaded with Nurr1 and Foxa2.

According to one exemplary embodiment, the viral vector may be an adeno-associated viral (AAV) or a lentiviral vector.

According to one exemplary embodiment, the inflammatory neurologic disorder may include at least one selected from the group consisting of Alzheimer's disease, Parkinson's disease, multiple systemic atrophy, amyotrophic lateral sclerosis (ALS), cerebral infarction, vertebral damage, neuropathic pain, and complex region pain syndrome (CRPS).

All the other contents disclosed above for the composition for preventing or treating an inflammatory neurologic disorder may also be directly or indirectly applied to the method of preventing or treating an inflammatory neurologic disorder without limitation.

Hereinafter, the present invention will be described in detail with reference to examples thereof. However, it should be understood that the following examples are just preferred examples for the purpose of illustration only and is not intended to limit or define the scope of the invention. The following examples described herein are provided in order to make the present invention more comprehensive and complete and provide the scope of the present invention to those skilled in the art to which the present invention belongs and thus will be defined by the appended claims equivalents thereof.

EXAMPLES

[Materials and Methods]
1. Cell Culture
mDA Neuron-Enriched Culture

Figure 2:
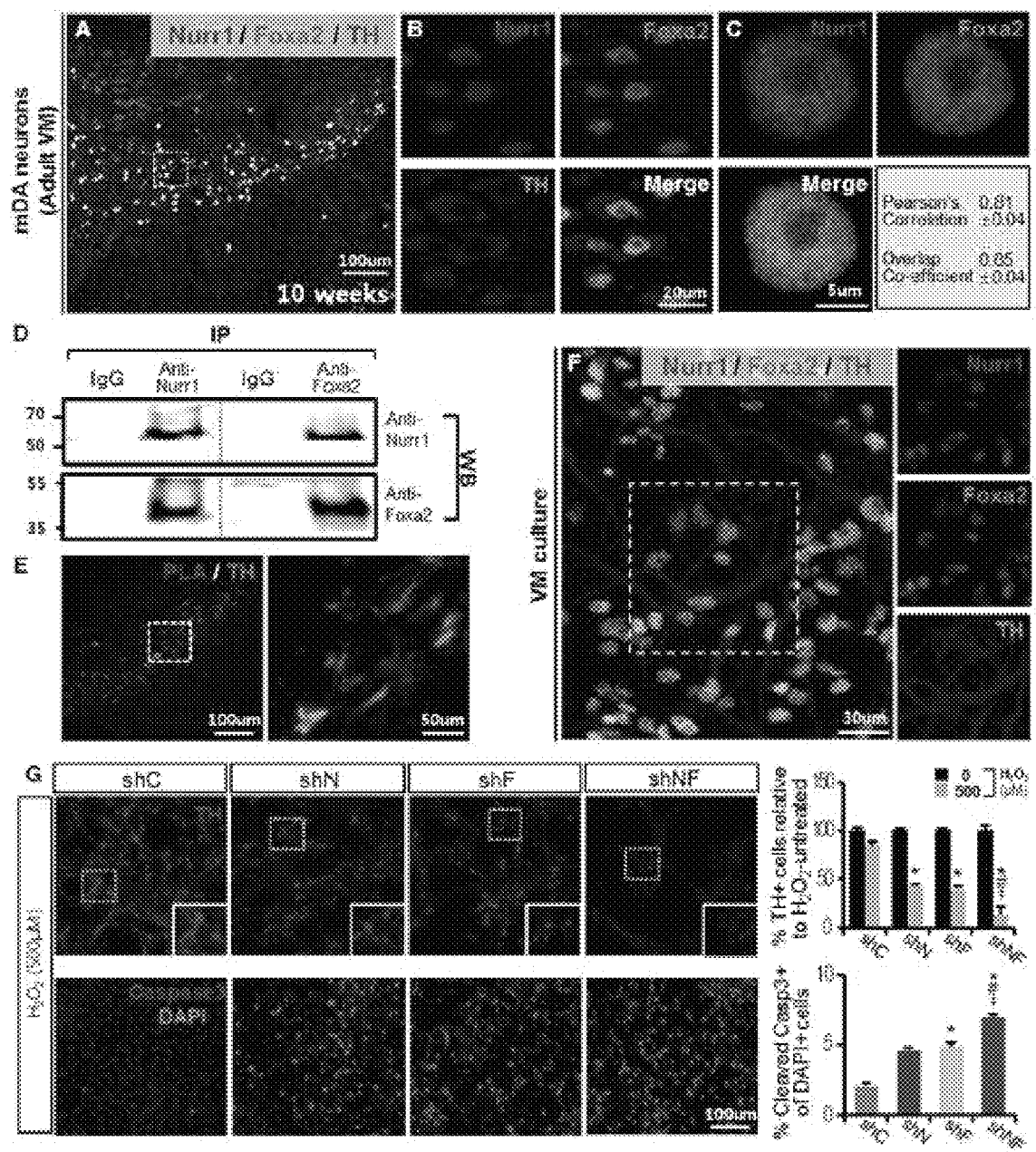
FIG. 2 shows that Nurr1 and Foxa2 physically and functionally interact to protect mDA neurons from toxic insult [A to C: Co-localization of Nurr1 and Foxa2 proteins in mDA neurons of the adult mouse midbrain. Representative confocal sections of the ventral midbrain (A) stained with antibodies specific for TH, Nurr1, and Foxa2. The midbrains of mice (10 weeks old) were cryosectioned, and stained images were taken using a confocal microscope with z-stacks through the section thickness (12 µm). Shown in (B) are individual and merged images of TH, Nurr1, and Foxa2 staining of the boxed area in (A) at higher magnifications. Representative images of a single nucleus from a TH+mDA neuron of an adult midbrain section (c) co-stained with Nurr1 (red) and Foxa2 (green). Co-localization of Nurr1 and Foxa2 in the merged images was assessed by Pearson's correlation and overlap coefficient values (n=4, right/low quadrant in C). D: Immunoprecipitation (IP) assay for Nurr1 and Foxa2 protein binding. The ventral part of midbrains was dissected from a 10-week-old mouse, lysed, and subjected to IP. Nurr1/Foxa2 protein binding was detected by WB analysis using an anti-Foxa2 antibody in immunoprecipitates generated with an anti-Nurr1 antibody (left), as well as by an anti-Nurr1 WB assay on immunoprecipitates using an anti-Foxa2 antibody (right). E: Physical interaction between Nurr1 and Foxa2 was further assessed by a proximity ligation assay (PLA). The SN area of a midbrain section (10 weeks old) was subjected to a PLA reaction and counterstained for TH. The boxed area in the left panel exhibiting the physical Nurr1/Foxa2 interaction (red) in TH+DA neurons (green) is enlarged in the right panel. F and G: Knockdown of Nurr1 and Foxa2 synergistically aggravates $H_2O_2$-induced cell death of mDA neurons in cultures. A representative image for Nurr1- and Foxa2-coexpressing mDA neurons (F) used in a loss-of-function study. Shown in right panels are the individual Nurr1-, Foxa2-, and TH-stained cells of the boxed area. Nurr1- and Foxa2-coexpressing mDA neurons were formed after 9 days of differentiation in VM-NPC cultures in vitro, and transduced with lentiviruses expressing shNurr1 (shN), shFoxa2 (shF), shN+shF (shNF), or shControl (shC). After three days, the cultures were treated with $H_2O_2$ (500 µM) for 8 hours, cells positive for TH (upper panel) were counted, and cleaved (activated) caspase-3 cells (lower panel) are counted on the following day (G). Insets, high-power TH+ cell images of the boxed areas. Significantly different from the control (shC)*, shF at P<0.05, n=5 culture wells in each group. P-values: 0.038 (shN*), 0.026 (shF*), 0.013 (shNF*), 0.036 (shNF#), and 0.042 (shNF‡) for the % $TH^+$ cells; 0.043 (shF*), 0.037 (shNF*), 0.019 (shNF#), and 0.029 (shNF‡) for the percent cleaved caspase-3-positive cells; one-way ANOVA followed by a Bonferroni post hoc test].

Midbrain dopamine (mDA) neurons expressing endogenous Nurr1 and Foxa2 were derived from a short-term expanded ventral midbrain-derived neural progenitor cell (VM-NPC) culture method, as described in the previous article (Yi S H, He X B, Rhee Y H, Park C H, Takizawa T, Nakashima K, Lee S H (2014) Foxa2 acts as a co-activator potentiating expression of the Nurr1-induced DA phenotype via epigenetic regulation. Development 141: 761-772). NPCs derived from the VMs of mouse embryos (imprinting control region, ICR) of pregnant mice at embryonic day 10.5 were expanded in vitro for 3 days in a serum-free N2 medium supplemented with a mitogen basic fibroblast growth factor (bFGF; 20 ng/ml; R&D Systems, Minneapolis, Minn.) and an epithelial growth factor (EGF; 20 ng/ml; R&D Systems), and then induced to differentiate by withdrawing the mitogens. Cells were BrdU-pulsed by treating the cells with BrdU (10 μM, Sigma, St. Louis, Mo.) for 16 hours prior to immunostaining with anti-BrdU and anti-TH antibodies. After 6-10 days, 10-20% of the total cells were mDA neurons expressing mature neuron-type and midbrain-type DA neuron-specific markers (FIG. 2F). In gain-of-function analysis for Nurr1 and Foxa2, primary cultures of DA neurons were established from mouse VM tissue. Briefly, VM tissues of the mice at embryonic days 13 to 14 were triturated to single cells with trypsin-EDTA and plated culture dishes pre-coated with poly-D-lysine (PDL; 25 μg/ml; Sigma, St. Louis, Mo.) in neurobasal medium (Life Technologies, Carlsbad, Calif.) supplemented with B27 and L-glutamine (Life Technologies). Ara-C (10 μM; Sigma) was added for days 3 to 5 to eliminate proliferating glial cells.

Glial Cell Culture

Methods of primarily culturing a mixture of astrocytes and microglial cells were derived from the VMs of mouse (ICR) pups on the postnatal day 1 using the protocols of methods disclosed in the previously published articles (Saura J., 2007). In brief, VMs were removed and triturated in a Dulbecco's modified Eagle's medium (DMEM; Life Technologies) containing 10% fetal bovine serum (FBS; HyClone, Logan, Utah), and the cells were plated on 75 cm$^2$ T-flasks. When cell confluence reached 80-90%, the glial cells were harvested with 0.1% trypsin and prepared for use by plating on PDL-coated culture surfaces. Pure astrocytes were isolated from mouse VMs on postnatal days 5-7 and cultured in an astro-medium (Heinrich C, Gascon S, Masserdotti G, Lepier A, Sanchez R, Simon-Ebert T, Schroeder T, Gotz M, Berninger B (2011) Generation of subtype-specific neurons from postnatal astroglia of the mouse cerebral cortex. Nat Protoc 6: 214-228). After the microglial cells were removed by gentle shaking, the cells were harvested, and re-plated on PDL-coated culture dishes. BV2 microglial cells were cultured in DMEM supplemented with 10% FBS (Blasi E, Barluzzi R, Bocchini V, Mazzolla R, Bistoni F (1990) Immortalization of murine microglial cells by a v-raf/v-myc carrying retrovirus. J Neuroimmunol 27: 229-237).

Mixed mDA Neuron and Glial Cells Culture mDA neurons primarily cultured from the mouse VMs (total cells: $8\times10^4$ cells/well) at the embryonic days 13-14 were plated on astrocyte-microglial beds ($2\times10^4$ cells/well in 24-well plates) and cultured in a neurobasal medium containing B27+L-glutamine (Life Technologies).

2. Virus Production

Lentiviral vectors expressing Nurr1 or Foxa2 under the control of a CMV promoter were generated by inserting the respective cDNAs into a multi-cloning site of pCDH (System Biosciences, Mountain View, Calif.). pGIPZ-shNurr1 and pGIPZ-shFoxa2 lentiviral vectors were purchased from Open Biosystems (Rockford, Ill.). The empty backbone vectors (pCDH or pGIPZ) were used as negative controls. The lentiviruses were produced and used to transduce in vitro cultures as described above (Yi S H, He X B, Rhee Y H, Park C H, Takizawa T, Nakashima K, Lee S H (2014) Foxa2 acts as a co-activator potentiating expression of the Nurr1-induced DA phenotype via epigenetic regulation. Development 141: 761-772). Titers of the lentiviruses were determined using a QuickTiter™ HIV Lentivirus quantitation kit (Cell Biolabs, San Diego, Calif.), and 2 ml of 6 cm dishes or 200 µl of wells (a 24-well plate) with $10^6$ transducing units (TU)/ml (60-70 ng/ml) were used for each transduction reaction. To induce in vivo expression by stereotaxic injection, AAVs expressing Nurr1 or Foxa2 [tagged with hemagglutinin (HA)] under the control of the CMV promoter were generated by subcloning the respective cDNAs into a pAAV-MCS vector (Addgene, Cambridge, Mass.). To assess the expression efficiency of a transgene, GFP-expressing AAVs were also generated. Packaging and production of the AAVs (serotype 2) were performed by the Korea Institute of Science and Technology (Seoul, Korea). AAV titers were determined using a QuickTiter™ AAV quantitation kit (Cell Biolabs). Co-expression studies were carried out by infecting cells with mixtures of individual viral preparations (1:1, v:v).

3. Preparation of Glial Cell-Conditioned Medium

Primary glia cell cultures (astrocytes+microglial cells) expressing Nurr1+Foxa2, Nurr1 alone, Foxa2 alone, and the empty control were prepared by lentiviral transduction. For co-expression of Nurr1+Foxa2, lentiviruses expressing each transgenes separately were mixed at a ratio of 1:1 (v:v) and added to cultures. The total volume and titer of the lentiviruses in the cultures expressing Nurr1 or Foxa2 alone were adjusted to be same as those of the co-transduced cultures by adding control viruses. A fresh medium was added 3 days after transduction, and a medium conditioned in the transduced glial cells was taken twice with an interval of 3 days. The conditioned media (CM) were filtered at 0.45 µM and stored at −80° C. until use.

4. Immunostaining

Cultured cells and cryosectioned brain slices were stained with the following primary antibodies: Nurr1 (1:500, rabbit, E-20, Santa Cruz Biotechnology, Dallas, Tex. and 1:1,000, mouse, R&D Systems); Foxa2 (1:500, goat, Santa Cruz Biotechnology); TH (1:250, rabbit, Pel-Freez, Rogers, Ark.); GFP (1:2,000, rabbit, Life Technologies); Iba-I (1:200, rabbit, Wako, Osaka, Japan); GFAP (1:200, mouse, MP Biomedicals, Santa Ana, Calif.); S100β (1:1,000, mouse, Sigma); TuJ1 (1:1,000, mouse, rabbit, Covance, Denver, Colo.); microtubule-associated protein 2 (MAP2; 1:200, mouse, Sigma); NeuN (1:200, mouse, Chemicon, Temecula, Calif.); DA transporter (DAT, 1:500, rabbit, Abcam, Cambridge, Mass.); vesicular monoamine transporter 2 (VMAT2; 1:500, rabbit, Pel-Freeze); Pitx3 (1:200, rabbit, Life Technologies); Lmx1a (1:2,000, rabbit, Millipore, Pittsburgh, Pa.); Nrf2 (1:200, rabbit, Santa Cruz Biotechnology); HA (1:200, Upstate Biotechnology, Lake Placid, N.Y., USA); cleaved caspase-3 (1:500, mouse, Cell Signaling Technology, Beverly, Mass.); and BrdU antibody (AbD Serotec, Kidlington, UK). Secondary antibodies tagged with Cy3, Cy5 (Jackson Immunoresearch Laboratories, West Grove, Pa.) or Alexa488 (Life Technologies) were used for visualization, and immunoreactive cells were analyzed under a fluorescence microscope (Leica, Heidelberg, Germany) or a confocal microscope (Leica PCS SP5). Co-localization of Nurr1 and Foxa2 proteins in TH+ DA neuronal nuclei was assessed by Pearson's correlation and overlap coefficient values using a Just Another Colocalization Plugin (JACoP) of ImageJ (NIH, Bethesda, Md.). In certain cases, TH-immunoreactive cells and fibers in midbrain and striatal sections were visualized by peroxidase-based colorimetric staining using a DAB substrate kit (Vector Laboratories, Burlingame, Calif.). Nissl staining has been done using NeuroTrace® 435/455 blue fluorescent kit (Molecular Probes, Eugene, Oreg.) based on the manufacture's protocol.

5. Messenger RNA Expression Analysis

Total RNA preparation, cDNA synthesis, and RT-PCRs were carried out using conventional methods. Real-time PCR was performed in a CFX96™ Real-Time System using iQ™ SYBR green supermix (Bio-Rad, Hercules, Calif.). Gene expression values were normalized to those of GAPDH. Primers information is listed in the following Table 1. High-throughput gene expression profiling for oxidative stress genes was done using a mouse oxidative stress PCR array (Cat. 330231 PAMM-065ZA) using an $RT^2$ Profiler PCR Array® (Qiagen, Gaithersburg, Md.).

TABLE 1

| Gene symbol | Sequence |
| --- | --- |
| TNF-α (tumor necrosis factor, alpha) | F: CGT CAG CCG ATT TGC TAT CT (SEQ ID NO: 1)<br>R: CGG ACT CCG CAA AGT CTA AG (SEQ ID NO: 2) |
| IL-1β (interlukin 1, beta) | F: GCC CAT CCT CTG TGA CTC AT (SEQ ID NO: 3)<br>R: AGG CCA CAG GTA TTT TGT CG (SEQ ID NO: 4) |
| iNOS (inducible nitric oxide synthase) | F: CCT CCT TTG CCT CTC ACT CTT C (SEQ ID NO: 5)<br>R: AGT ATT AGA GCG GTG GCA TGG T (SEQ ID NO: 6) |

TABLE 1-continued

| Gene symbol | Sequence |
| --- | --- |
| IL-6 (interleukin 6) | F: ATG GAT GCT ACC AAA CTG GAT (SEQ ID NO: 7)<br>R: TGA AGG ACT CTG GCT TTG TCT (SEQ ID NO: 8) |
| BDNF (brain-derived neurotropic factor) | F: GTG ACA GTA TTA GCG AGT GGG (SEQ ID NO: 9)<br>R: GGG TAG TTC GGC ATT GC (SEQ ID NO: 10) |
| NT3 (neurotrophin 3) | F: GGT CAG AAT TCC AGC CGA TGA (SEQ ID NO: 11)<br>R: GGC ACA CAC ACA GGA AGT GTC (SEQ ID NO: 12) |
| GDNF (glial cell line derived neuotrophic factor) | F: CGC CCG CCG AAG ACC ACT CC (SEQ ID NO: 13)<br>R: GTC GAA GGC GAC CGG CCT GC (SEQ ID NO: 14) |
| SHH (sonic hedgehog) | F: AAA AGC TGA CCC CTT TAG CC (SEQ ID NO: 15)<br>R: TGC ACC TCT GAG TCA TCA GC (SEQ ID NO: 16) |
| IGF-1 (insulin-like growth factor 1) | F: TGC TCT TCA GTT CGT GTG (SEQ ID NO: 17)<br>R: ACA TCT CCA GTC TCC TCA G (SEQ ID NO: 18) |
| IGF-2 (insulin-like growth factor 2) | F: ACA ACT TCG ATT TGA ACC ACA TTC (SEQ ID NO: 19)<br>R: GAG AGC TCA AAC CAT GCA AAC T (SEQ ID NO: 20) |
| EPO (erythropoietin) | F: GAG GCA GAA AAT GTC ACG ATG (SEQ ID NO: 21)<br>R: CTT CCA CCT CCA TTC TTT TCC (SEQ ID NO: 22) |
| TRX (thioredoxin) | F: CGT GGT GGA CTT CTC TGC TAC GTG GTG (SEQ ID NO: 23)<br>R: GGT CGG CAT GCA TTT GAC TTC ACA GTC (SEQ ID NO: 24) |
| TGF-β (transforming growth factor, beta) | F: CAC CGG AGA GCC CTG GAT A (SEQ ID NO: 25)<br>R: TGT ACA GCT GCC GCA CAC A (SEQ ID NO: 26) |
| IRF4 (interferon regulatory factor 4) | F: GCA GCT CAC TTT GGA TGA CA (SEQ ID NO: 27)<br>R: CCA AAC GTC ACA GGA CAT TG (SEQ ID NO: 28) |
| Arg1 (arginase 1) | F: GTG AAG AAC CCA CGG TCT GT (SEQ ID NO: 29)<br>R: CTG GTT GTC AGG GGA GTG TT (SEQ ID NO: 30) |
| CD206 | F: ATG CCA AGT GGG AAA ATC TG (SEQ ID NO: 31)<br>R: TGT AGC AGT GGC CTG CAT AG (SEQ ID NO: 32) |
| S100β (S100 calcium binding protein B) | F: GGC GGC AAA AGG TGA CCA GGA (SEQ ID NO: 33)<br>R: GCC CTC ATG TCT GCC ACG GG (SEQ ID NO: 34) |
| RAGE (receptor for advanced glycation endproducts) | F: CAG CAT CAG GGT CAC AGA AA (SEQ ID NO: 35)<br>R: CTG GTT GGA GAA GGA AGT GC (SEQ ID NO: 36) |

TABLE 1-continued

| Gene symbol | Sequence |
| --- | --- |
| GFAP (glial fibrillary acidic containing 3) | F: GC GAC CTC ACA GAC GTT GCT (SEQ ID NO: 37)<br>R: AGG CTG GTT TCT CGG ATC TGG (SEQ ID NO: 38) |
| Jmjd3 (jumonji domain containing 3) | F: AGT CCA TTG TGC CCA TGA TT (SEQ ID NO: 39)<br>R: GCA GTA GTA GGC AGG CTC GT (SEQ ID NO: 40) |
| GAPDH (glyceraldehyde-3-phosphate dehydrogenase) | F: GCT CCT CCT GTT CGA CAG TCA (SEQ ID NO: 41)<br>R: ACC TTC CCC ATG GTG TCT GA (SEQ ID NO: 42) |

6. Immunoprecipitation (IP) and Western Blot (WB) Analysis

Interaction between Nurr1 and Foxa2 (in mouse VM tissues at 10 weeks of age) was assessed by an IP. Tissues were lysed in IP lysis buffer (Thermo Scientific, Waltham, Mass.) supplemented with protease inhibitors. Lysates were incubated with an anti-Nurr1 antibody (1:1,000, mouse, R&D Systems) or an anti-Foxa2 antibody (1:1,000, goat, Santa Cruz Biotechnology) at 4° C. for 18-24 hours. The mixtures were shaken with magnetic beads (Life Technologies) at room temperature for 1-2 hours. After washing, immunoprecipitated proteins were eluted in a sample buffer and subjected to a Western blot analysis using an anti-Foxa2 antibody (1:1,000, goat, Cell Signaling Technology) or an anti-Nurr1 antibody (1:500, mouse, R&D Systems).

7. In Situ Proximity Ligation Assay (PLA)

The Nurr1/Foxa2 protein interaction in the VM was further analyzed by PLA. As described above, frozen slices of mouse VM tissues (10 weeks old) were treated with primary anti-Nurr1 (1:1,000, mouse, R&D Systems) and Foxa2 antibodies (1:1,000, goat, Cell Signaling Technology) and followed by a secondary antibody, ligation, polymerization, and detection using an in situ PLA assay kit (Olink Bioscience, Uppsala, Sweden), as described previously (Yi et al., 2014).

8. Measurement of Reactive Oxygen Species (ROS), Nitrogen Oxide (NO), and Arginase Activity To measure intracellular ROS levels, cells were incubated with 10 μM of 5-(and -6)-chloromethyl-2',7'-dichlorodihydrofluorescein diacetate [CM-$H_2$DCF-DA (hereinafter referred to as DCF); Life Technologies] for 10 minutes. The cells were then washed with D-PBS (in mM: 2.68 KCl, 1.47 $KH_2PO_4$, 136.89 NaCl, and 8.1 $Na_2HPO_4$), and fluorescence images and phase-contrast images were taken using an Olympus (IX71, Hicksville, N.Y.). An amount of nitrite formed from NO was measured by mixing a culture medium (50 μl) with an equal volume of a Griess reagent (0.1% naphthylethylene diamine, 1% sulfanilamide, and 2.5% $H_3PO_4$). The optical density was measured at 540 nm. The arginase activity was measured with a QuantiChrom Arginase assay kit (Bioassay Systems, Hayward, Calif.) according to the manufacturer's instructions.

9. Animal Care and Experiments

All procedures for animal experiments were approved by the Institutional Animal Care and Use Committee (IACUC) at the Hanyang College of Medicine under the approval number 2013-0153A. Animals were housed in a specific pathogen-free barrier facility with a 12-hours light/dark cycle and maintained on standard chow (5053 PicoLab® Rodent Diet 20). The sizes of the animals for our experiments were determined according to our in vitro assays and a pilot test without previous statistical calculation. The experiments were performed in accordance with the NIH guideline. To minimize bias, behavioral assays have mostly been assessed by two experimenters in a blinded-experiment fashion.

10. Stereotaxic AAV Injection into MPTP-Treated PD Mice

Male mice (10-14 weeks old, ICR) received intraperitoneal (i.p.) injections of MPTP (20 mg/kg) once daily for five consecutive days. Three days prior to, or 2 days after, the first MPTP injection, mixtures of Nurr1-AAV (1 μl)+control-AAV (1 μl) (2 μl; $10^{12}$ vg (virus genome)/μl for an Nurr1 group), Foxa2-AAV (1 μl)+control-AAV (1 μl) (2 μl; $10^{12}$ vg/μl for a Foxa2 groups), Nurr1-AAV (1 μl)+Foxa2-AAV (1 μl) ((2 μl; $10^{12}$ vg/μl for an Nurr1+Foxa2 group), or control group-AAV (2 μl; $10^{12}$ vg/μl for the, control group only) were injected into ventral midbrains (3.3 mm posterior to the bregma; ±1.2 mm lateral to the midline; −4.6 mm ventral to the dura) over 3 minutes under anesthesia induced by Zoletil 50 (0.1 mg/kg) mixed with Rompum (93.28 μg/kg). A needle (Gauge 26) was left in an injection site for 5 to 10 minutes after completion of each injection, and removed slowly. When inaccurate injection at the SN positions were confirmed, the mice were excluded from the analysis.

11. Histological Measurement of TH-Immunoreactive Cells

Four weeks to 1 year after the AAV injection, animals were anesthetized and intracardially perfused with 4% paraformaldehyde dissolved in PBS. Brains were removed, immersed in 30% sucrose dissolved in PBS overnight, and then sliced using a freezing microtome (CM 1850; Leica, Wetzlar, Germany). Midbrain and striatal sections (30 μm thick) were subjected to TH immunohistochemistry, as described above. The total number of mDA neurons in the right and left sides of the midbrain was obtained by counting TH-immunoreactive cells throughout the midbrain (a total of 11-14 sections counted for each animal) The Abercrombie correction factor=n×T/(T+DA wherein N is the actual number of cells, n is the number of nuclear profiles, T is the section thickness (30 μm), and D is the average diameter of nuclei, was used to compensate for double counting in adjacent sections.

12. Behavior Tests

Apomorphine-Induced Rotation Test

Apomorphine (Sigma) was subcutaneously injected at a dose of 0.5 mg/kg and rotation was monitored for 60 minutes. The results are expressed as net turns/60 min Cylinder Test Mice were placed in a small transparent cylinder (having a height of 15.5 cm and a diameter of 12.7 cm), and, the numbers of right and left forelimbs contact with the wall of the arena while rearing were recorded for 3 minutes.

Pole Test

Animals were placed head upwards on top of a vertical wooden pole 50 cm in length (diameter, 1 cm). A base of the pole was placed in the home cage. Once placed on the pole, animals oriented themselves downward and descended in the length of the pole back into their home cage. All of the animals were trained for 2 days, the training of which consists of five trials for each session. On the test day, the animals received five trials, and the time to orient downward was measured.

Challenging Beam Traversal Test

Motor performance was measured using a novel beam test adapted from traditional beam-walking tests. Briefly, the beam (length, 1 m) started at a width of 3.5 cm and gradually narrowed to 0.5 cm in 1-cm increments. Animals were trained to traverse the length of the beam, starting at the widest section and ending at the narrowest section for 2 days before actual testing. Times required for the animals to traverse the beam were measured.

Locomotion Test

A 40-cm square cage with peripheral and central areas was used for a locomotion test. Mice were placed in the center of an open field and allowed to freely explore an apparatus for 20 minutes while being tracked by a video-recording system. After the test, each mouse was returned to its home cage, and the open field was cleaned with 70% ethyl alcohol and permitted to dry between tests. To assess the process of habituation to the novelty of the arena, mice were exposed to the apparatus for 20 minutes on two consecutive days for a statistical analysis.

13. Cell Counting and Statistical Analysis

Immunostained and DAPI-stained cells were counted in 10-20 random areas of each culture coverslip using an eyepiece grid at a magnification of 200× or 400×. Data are expressed as the mean±SEM of 3 to 10 independent cultures. In the present invention, normal distribution of the data was confirmed by Kolmogorov-Smirnov test. For every figure, statistical tests were justified as appropriate. Statistical comparisons were made using Student's t-test (unpaired or paired) or one-way ANOVA, followed by Bonferroni post hoc analysis using SPSS® (Statistics 21; IBM Inc.). The n, P-values, and statistical analysis methods are indicated in the figure legends.

14. In Vivo Test

Although the in vitro data clearly suggested a Nurr1+Foxa2 effect in M1-to-M2 polarization of glial cells, it remains to be identified if the similar Nurr1+Fox2-mediated effects could be replicated after transplantation in the host brain in vivo, where the grafted cells are inevitably exposed to hostile inflammatory/immunogenic environments and interact with endogenous cells such as glia, neuronal cells, and peripheral blood cells entered through disrupted BBB (Blood-Brain-Barrier) during cell injection process. Especially, glia after brain injury can be reactivated into the detrimental M1 phenotype at delayed phase of injuries (Eddleston, M., and Mucke, L. (1993). Molecular profile of reactive astrocytes—implications for their role in neurologic disease. Neuroscience 54, 15-36; Hu, X., Li, P., Guo, Y., Wang, H., Leak, R. K., Chen, S., Gao, Y., and Chen, J. (2012). Microglia/macrophage polarization dynamics reveal novel mechanism of injury expansion after focal cerebral ischemia. Stroke; a journal of cerebral circulation 43, 3063-3070; Pekny, M., and Pekna, M. (2014). Astrocyte reactivity and reactive astrogliosis: costs and benefits. Physiol Rev 94, 1077-1098), raising concerns that astroglia grafted might also be turned into harmful M1 phenotype after transplantation. Thus, we tested if transplantation of Nurr1+Foxa2-expressing astrocytes can correct harmful brain environment and thus establish a neurotrophic therapeutic environment.

Astrocytes were cultured from ventral midbrain (VM) on postnatal day 5-7 and transduced with Nurr1+Foxa2-expressing lentiviruses (NF-astrocyte) or lentiviruses carrying mock control vector (control-astrocyte). The astrocytes (3 ul, $0.5 \times 10^5$ cells/ul) were transplanted intro striatum of rats. The animals were sacrificed at 1 month of post-transplantation and grafted brains were sliced with 1 mm thickness, and 8-12 regions of the graft-host interface (ca 2×2 mm)/graft were dissected and subjected to qPCR analysis.

[Results]

Nurr1 and Foxa2 Interact to Protect mDA Neurons Against Toxic Insult

Confocal microscopic analyses on the midbrains of adult mice (10 weeks old) demonstrated that Nurr1 and Foxa2 were present in the nuclei of virtually all tyrosine hydroxylase (TH)-positive mDA neurons (FIGS. 2A and 2B) having a high co-localization indices (FIG. 2C). In immunoprecipitation (IP) experiments using midbrain lysates of 10-week-old mice, Foxa2 was detected in Nurr1 antibody precipitates, and Nurr1 was also detected in Foxa2 antibody precipitates (FIG. 2D), demonstrating physical binding between Nurr1 and Foxa2 in the adult midbrains. Close physical interaction of these two proteins was confirmed by an in situ proximity ligation assay (PLA), which allows visualization of protein-protein binding by red fluorescence (554 nm) emanating from two proteins in close proximity (FIG. 2E). These findings collectively suggest an interplay between Nurr1 and Foxa2 that promotes functions of mDA neurons in the adult midbrain, like those seen in the developing midbrain.

Midbrain-type DA neurons co-expressing endogenous Nurr1 and Foxa2 were generated by in vitro differentiation of neural precursor cells (NPCs) derived from the ventral midbrain (VM) (FIG. 2F). To examine the roles of Nurr1 and Foxa2, differentiated cultures were treated with silencing small hairpin RNAs (shRNAs) for these factors. The shRNA treatments were effective in down-regulating the expression of Nurr1 and Foxa2. mRNA levels of Nurr1 (relative to the shControl) were 1±0.03, 0.43±0.01, 0.84±0.03, and 0.28±0.004 in the presence of shControl, shNurr1, shFoxa2, and shNurr1+shFoxa2, respectively, and the corresponding Foxa2 mRNA levels were 1±0.05, 0.89±0.03, 0.45±0.06, and 0.33±0.02 (n=3 PCRs for each group). These results are consistent with a positive regulatory loop for the expression of Nurr1 and Foxa2 since the Nurr1 expression slightly decreased by the shFoxa2 treatment, and the Foxa2 expression was slightly decreased by the shNurr1 treatment. Most importantly, DA neuronal numbers synergistically decreased by Nurr1 and Foxa2 knockdown: $TH^+$ cells 3 days after the shRNA treatments were 1,235±17 (shControl), 816±13 (shNurr1), 805±14 (shFoxa2), and 276±7 cells/well (shNurr1+shFoxa2) (n=4 culture wells in each group), indicating that Nurr1 and Foxa2 cooperate in promoting mDA neuronal survival. Treatment with the free radical-producing chemical $H_2O_2$ caused mDA neuronal death. The loss of $TH^+$ mDA neurons in response to $H_2O_2$ increased in the cultures treated with shNurr1 or shFoxa2, this was accompanied by increased numbers of cells with cleaved (activated) caspase-3 (FIG. 2G). The effect of combined shNurr1+shFoxa2 treatment was even more dramatic. Indeed, although a few cells remained immunoreactive for TH in the cultures treated with shNurr1+shFoxa2, all had blunted or fragmented neurites (FIG. 2G inset), a neuronal aging and degenerative phenotype (Hof P R, Morrison J H (2004) The aging brain: morphomolecular senescence of cortical circuits. Trends Neurosci 27: 607-613). Due to the developmental roles of Nurr1 and Foxa2 in generation of mDA neurons, the observed effects of shNurr1+shFoxa2 might have been obtained by affecting mDA neurogenesis. However, the present inventors did not detect any new neuronal formation in the differentiated cultures and found that shNurr1 and shFoxa2 treatment did not alter the neurogenesis in a BrdU-pulsed experiment. Collectively, these findings suggest that Nurr1 and Foxa2 physically and functionally interact in mDA neurons to protect these neurons from toxic insults, and their neuroprotective effects are probably mediated in a cell-autonomous manner since these factors are actually present in the neurons.

Figure 3:
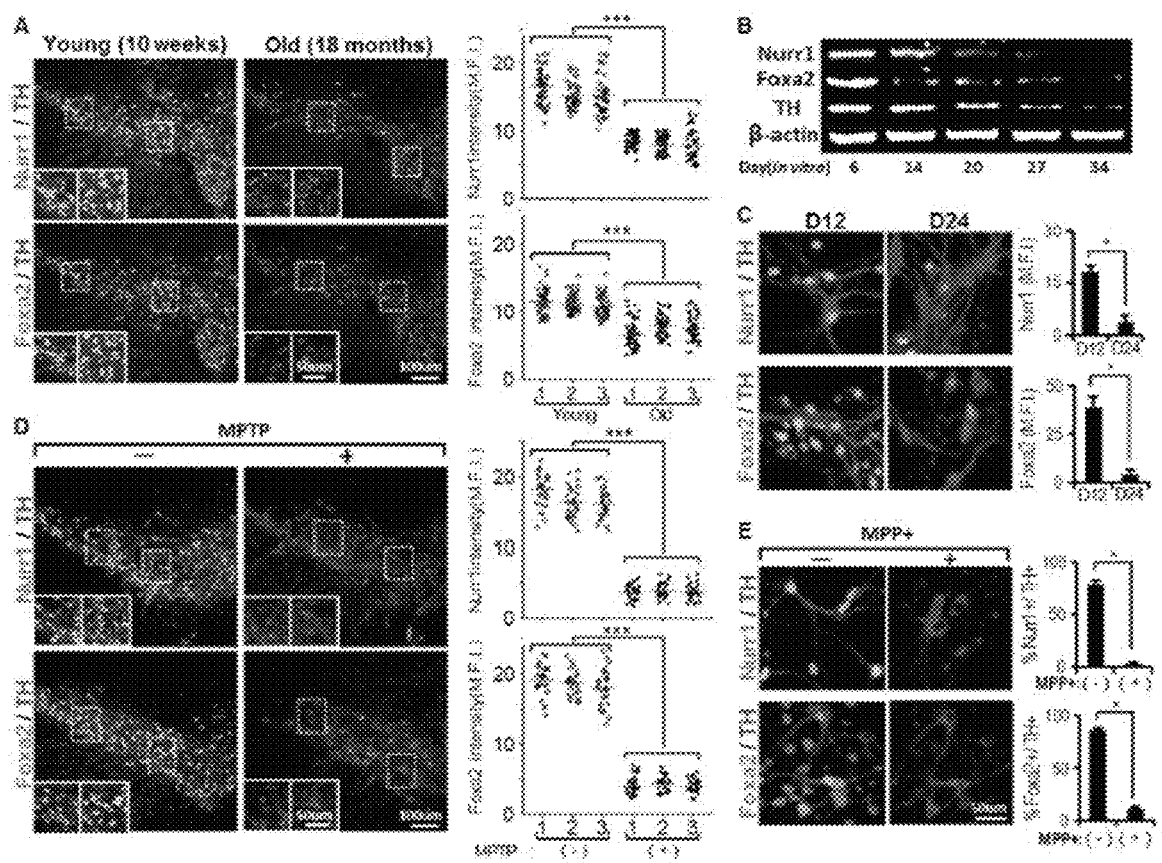
FIG. 3 shows that Nurr1 and Foxa2 in mDA neurons are reduced during an aging and degeneration [A to C: Levels of Nurr1 and Foxa2 proteins in mDA neurons decrease in the midbrains of old mice in vivo (A) and in vitro after long-term culture (B and C). (A) The levels of Nurr1 and Foxa2 proteins were compared in individual mDA neurons of the midbrains of young mice (10 weeks old) and old mice (18 months old) of the same mouse strain (C57BL/6, male). All of the midbrain sections were immunofluorescently co-stained with Nurr1/TH (upper panel) and Foxa2/TH (lower panel) under identical conditions, and the levels of Nurr1 and Foxa2 proteins were determined in individual $TH^+$ mDA neurons by measuring mean fluorescence intensities (MFI) using LAS image analysis (Leica). Dots in the graphs represent the Nurr1 and Foxa2 MFI values of individual $TH^+$ DA neurons in the SN of each animal. The average MFI values (indicated by horizontal lines) of three animals from each group were compared (***P=5.25E-88 for Nurr1 intensity, 5.57E-40 for Foxa2 intensity, one-way ANOVA followed by a Bonferroni post hoc test). The levels of Nurr1 and Foxa2 proteins were also quantified in cultured mDA neurons over 6 to 34 days in vitro by Western blotting (B) and by immunocytochemical analysis (C). Significantly lower MFI values on the day 24 of culture (D24) compared to D12 at *P=0.027 (Nurr1), *P=0.012 (Foxa2), n=60 to 70 $TH^+$ cells from two cultures in each group; an unpaired Student's t-test. D and E: Loss of Nurr1 and Foxa2 expression in mDA neurons after treatment with a neurotoxin MPTP (or MPP+). Mice (10 weeks old) were treated with MPTP for 5 days as described in Materials and Methods. Three days after the last MPTP injection, levels of Nurr1 and Foxa2 proteins in the $TH^+$ mDA neurons of the MPTP-treated SN were compared with those in the mDA neurons of untreated mice (D) (***P=5.47E-103 for Nurr1 intensity, 1.53E-111 for Foxa2 intensity, one-way ANOVA followed by a Bonferroni post hoc test). Therapeutic effects of the neurotoxin were also determined in mDA neuron cultures treated with MPP+ (250 µM, 8 hours, E). *P=0.015 (% $Nurr1^+/TH^+$ cells), *P=0.018 (% $Foxa2^+/TH^+$ cells); an unpaired Student's t-test].

Levels of Nurr1 and Foxa2 Proteins Decrease in mDA Neurons During Aging and Degeneration Aging is a crucial predisposing factor for Parkinson's disease (PD). Interestingly, the levels of both Nurr1 and Foxa2 were significantly lower in the individual mDA neurons of the old mice (18 months old) than in their young counterparts (10 weeks old) (FIG. 3A). In agreement with this, the levels of Nurr1 and Foxa2 also gradually declined in the cultured mDA neurons during the late period of cultures (6-34 days after the onset of differentiation in vitro; FIG. 3B), ultimately giving rise to abundant $TH^+$ cells negative for Nurr1/Foxa2 (% $Nurr1^+$ of $TH^+$ cells: 90.5% at D12 versus 14.3% at D24 and % $Foxa2^+$ of $TH^+$ cells: 91.3% at D12 versus 12.9% at D24, FIG. 3C). These findings are consistent with a decreased Nurr1 levels in the SNs of the elderly and also imply that the loss of Foxa2 is an additional aspect of the aging process in the mDA neurons.

1-Methyl-4-phenyl-1,2,3,6-tetrahydropyridine (MPTP) and an active metabolite 1-methyl-4-phenylpyridinium (MPP+) specifically induce the degeneration of mDA neurons. A decline in levels of Nurr1 and Foxa2 proteins was evident in $TH^+$ mDA neurons of mice (10 weeks old) after MPTP treatment (FIG. 3D). The toxin-induced loss of Nurr1 and Foxa2 was also seen in the TH+ mDA neurons in vitro before any obvious loss of mDA neurons was detected (FIG. 3E). These findings taken together indicate that decrease in expression of Nurr1 and Foxa2 is manifestation of cellular aging and degeneration of mDA neurons, and thus overexpression of these factors might be a therapeutic option for protecting mDA neurons against a degenerative process in PD.

Figure 4:
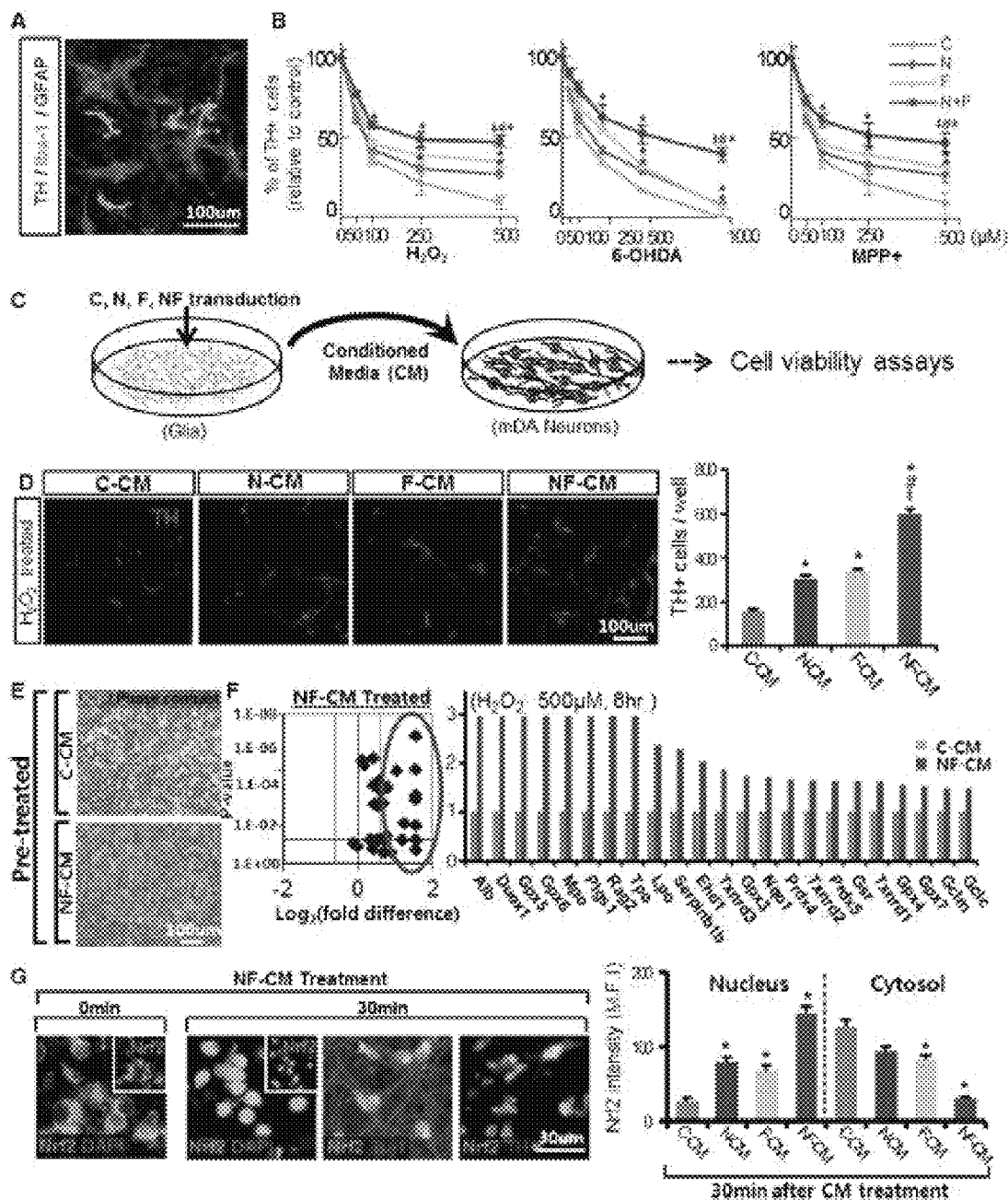
FIG. 4 shows that overexpression of Nurr1 and Foxa2 in glia neighbored to mDA neurons protects mDA neurons from toxic insults in vitro in a paracrine manner [A: Representative image for $TH^+$ (mDA neuron), $GFAP^+$ (astrocyte), and Iba-$1^+$ (microglia) cells in mDA neuron-glial cell cultures used in Nurr1 and Foxa2 gain-of-function experiments. B: mDA neuron-glia cultures transduced with Nurr1 and/or Foxa2 are resistant to toxic stimuli induced by $H_2O_2$ (50-500 µM), 6-OHDA (50-1,000 µM), or MPP+(50-500 µM). The mDA neuron-glial cell cultures were transduced with lentiviruses expressing Nurr1 (N), Foxa2 (F), Nurr1+Foxa2 (NF), or the control (C) and treated with a toxin for 8 hours. Viable $TH^+$ cells are counted on the following day. Percentages of $TH^+$ cells with respect to the respective toxin-untreated cultures are shown in the graphs. $TH^+$ cells of C, N, F, and NF were compared at the same concentrations of the toxins. Significantly different from the control (C)*, from N#, and from F‡ at P<0.05, n=10 cultures each; one-way ANOVA followed by a Bonferroni post hoc test. C and D: Overexpression of Nurr1 and Foxa2 in glial cells exerts neuroprotective roles on mDA neurons in a paracrine mode. Experimental scheme (C) to test the effects of paracrine factors released from Nurr1-/Foxa2-expressing glial cells. Mixed astrocytes microglial cell cultures (derived from VM tissue of mouse pups on the postnatal day 1) were transduced with N, F, NF, or C, and conditioned media (CM) are prepared from the transduced glial cells, and added to mDA neuron cultures. Two days after the CM treatment, $H_2O_2$ (500 µM, 8 hours)-mediated cell death is measured by counting viable TH+ cells (D). Significantly different from the control (C-CM)*, N-CM#, F-CM‡ at P<0.05. P-values: 0.031 (N-CM*), 0.021 (F-CM*), 0.017 (NF-CM*), 0.022 (NF-CM#), and 0.027 (NF-CM‡); one-way ANOVA followed by a Bonferroni post hoc test. E to G: NF-expressing glial cells secrete factors that reduce oxidative stress by inducing Nrf2-mediated antioxidant gene expressions. Oxidative stress was measured by oxidative stress indicator (DCF) staining (E). Primarily cultured mDA neurons were pre-treated with C-CM (upper panel) or NF-CM (lower panel) for 2 days, and then exposed to $H_2O_2$ (250 µM) in the presence of CM. After four hours, DCF staining was carried out. (F) Expression array for antioxidant genes. mDA neuron cultures were pre-treated with C-CM, N-CM, F-CM, or NF-CM for 2 days before exposure to 500 µM $H_2O_2$ for 8 hours, and mRNA expression levels of 39 antioxidant genes were evaluated using an RT2 PCR Profiler Array®. Volcano plot (left panel) demonstrating a tendency for increased expression of antioxidant genes in the mDA neuron cultures with NF-CM treatment. The pink lines indicate the threshold of 1.5-fold changes in gene expression. The 23 antioxidant genes up-regulated 1.5-fold (circled) by NF-CM treatment with respect to C-CM treatment are listed on the bar graph (right panel). (G) NF-CM treatment of mDA neurons activates cytosolic Nrf2 proteins (0 min) by inducing nuclear translocation (30 minutes). Levels of cytosolic and nuclear Nrf2 proteins (MFI) after 30 minutes of C-CM, N-CM, F-CM, and NF-CM treatments are shown on the graph. *P<0.05, n=50 to 60 cells in each group. P-values: 0.032 (N-CM*), 0.029 (F-CM*), 0.019 (NF-CM*) for the Nrf2 intensity in the nucleus, 0.029 (F-CM*), 0.039 (NF-CM*) for the Nrf2 intensity in the cytosol; one-way ANOVA followed by a Bonferroni post hoc test].

Overexpression of Nurr1 and Foxa2 Protects mDA Neurons Against Toxic Insults in mDA Neuron-Glial Cell Cultures To test a therapeutic potential of Nurr1/Foxa2 overexpression, the present inventors used primary mDA neuron-glial cell cultures derived from the mouse VM (FIG. 4A), which reflected the in vivo cellular composition and environment of the midbrain. The cultures were transduced with lentiviruses expressing Nurr1, Foxa2, Nurr1+Foxa2, or a control empty vector (control). Numbers of DA neurons at 5 days after the transduction (15 days in vitro, DIV) were significantly increased in the Nurr1- or Foxa2-transduced cultures. The number of viable DA neurons was the greatest after the transduction of Nurr1+Foxa2 (Control, 1,136±819; Nurr1, 1,533±19; Foxa2, 1,766±21; Nurr1+Foxa2, 1,939±22 cells/well, n=4 culture wells in each group). Numbers of $TH^+$ DA neurons decreased with increasing $H_2O_2$ dose. Introduction of Nurr1 and Foxa2 additionally or synergistically prevented the $H_2O_2$-induced loss of $TH^+$ cells (FIG. 4B, left). Nurr1 and Foxa2 exerted a similar protective effect against the parkinsonian toxins MPP+ and 6-hydroxydopamine (6-OHDA) (FIG. 4B, Middle and right).

Glial Cells Expressing Nurr1+Foxa2 Secrete Molecules that Protect mDA Neurons Via Nrf2-Mediated Anti-Oxidantion Most previous works have suggested that Nurr1 and Foxa2 in mDA neurons exert cell-autonomous cell survival/protective effects, and this view is supported by the knockdown experiments shown in FIG. 2G. However, lentivirus-mediated transgenes expression was detected in only in a few $TH^+$ DA neurons, but in many more $GFAP^+$ or $Iba-1^+$ glial cells, indicating that the cytoprotective effects observed in the gain-of-function experiments by the present inventors, at least, were not mediated by cell-autonomous actions of Nurr1 and Foxa2, but probably in an extrinsic manner by the glial cells expressing Nurr1 and Foxa2. This hypothesis is consistent with the study of Saijo K et al., (2009) [A Nurr1/CoREST pathway in microglia and astrocytes protects dopaminergic neurons from inflammation-induced death. Cell 137: 47-59], demonstrating a paracrine neuroprotective effect of Nurr1. To test a potential paracrine action, the present inventors transduced glial cells (astrocytes+microglial cells derived from midbrains) with Nurr1, Foxa2, Nurr1+Foxa2, or the control, and also added a medium conditioned in the glial cells to primary mDA neuron cultures (FIG. 4C). A conditioned medium (CM) from Nurr1-transduced glial cells (Nurr1-CM) and Foxa2-transduced glial cells (Foxa2-CM) exerted a neuroprotective effect (FIG. 4D). The neuroprotective effect by the CM prepared from Nurr1+Foxa2-transduced glial cells (Nurr1+Foxa2-CM) was more dramatic than those of Nurr1-CM and Foxa2-CM.

As shown in FIG. 4C, viruses expressing Nurr1 (N), Foxa2 (F), and Nurr1+Foxa2 (NF) were introduced into the cultured glial cells (viruses harboring an empty vector having no specified genes are introduced in the control (C)), conditioned media (CM) were collected at 2 days after the cultures, and dopaminergic neurons were treated with the CM. CMs collected from the glial cells expressing Nurr1, Foxa2, and Nurr1+Foxa2, compared to CM collected from control glia, showed effects of protecting dopaminergic neurons from damage caused by $H_2O_2$, and the effect of the CM collected from Nurr1+Foxa2-expressing glia was the greatest and greater than sum of the effects of Nurr1-CM plus Foxa2-CM, indicating that the Nurr1 and Foxa2 in glial cells has a synergistic therapeutic effect of protecting neurons via a paracrine mechanism since the synthesis/secretion of inflammatory factors (i.e., pro-inflammatory cytokines) is inhibited and the synthesis of neurotrophic factors increases when Nurr1 and Foxa2 are expressed in the glial cells, as shown in FIG. 1 (FIG. 4D).

Levels of reactive oxygen species (ROS) in $H_2O_2$-treated mDA neuron cultures were greatly reduced by a pretreatment with Nurr1+Foxa2-CM (FIG. 4E). In a super-array analysis, the expression patterns of antioxidant genes in the cultures treated with Nurr1-CM or Foxa2-CM were not greatly different from the cultures treated with control-CM. However, the expression of most of the tested antioxidant genes was increased by Nurr1+Foxa2-CM (FIG. 4F), indicating that the combined expression of Nurr1+Foxa2 in the glial cells is required to reduce oxidative stress in neighboring mDA neurons by inducing the expression of the antioxidant genes. Nuclear factor-erythroid 2-related factor 2 (Nrf2) is a master regulator of antioxidant defense via the scavenging of ROS, which acts by inducing the expression of antioxidant genes. Upon activation, cytoplasmic Nrf2 proteins were translocated to the nucleus where they bind to the antioxidant responsive element (ARE) and activate the transcription of a large array of antioxidant genes. The Nurr1+Foxa2-CM treatment rapidly and robustly triggered the nuclear localization of Nrf2 in the mDA neuron cultures (FIG. 4G).

Molecules Responsible for the Paracrine Neuroprotective Actions of Nurr1 and Foxa2

Figure 5:
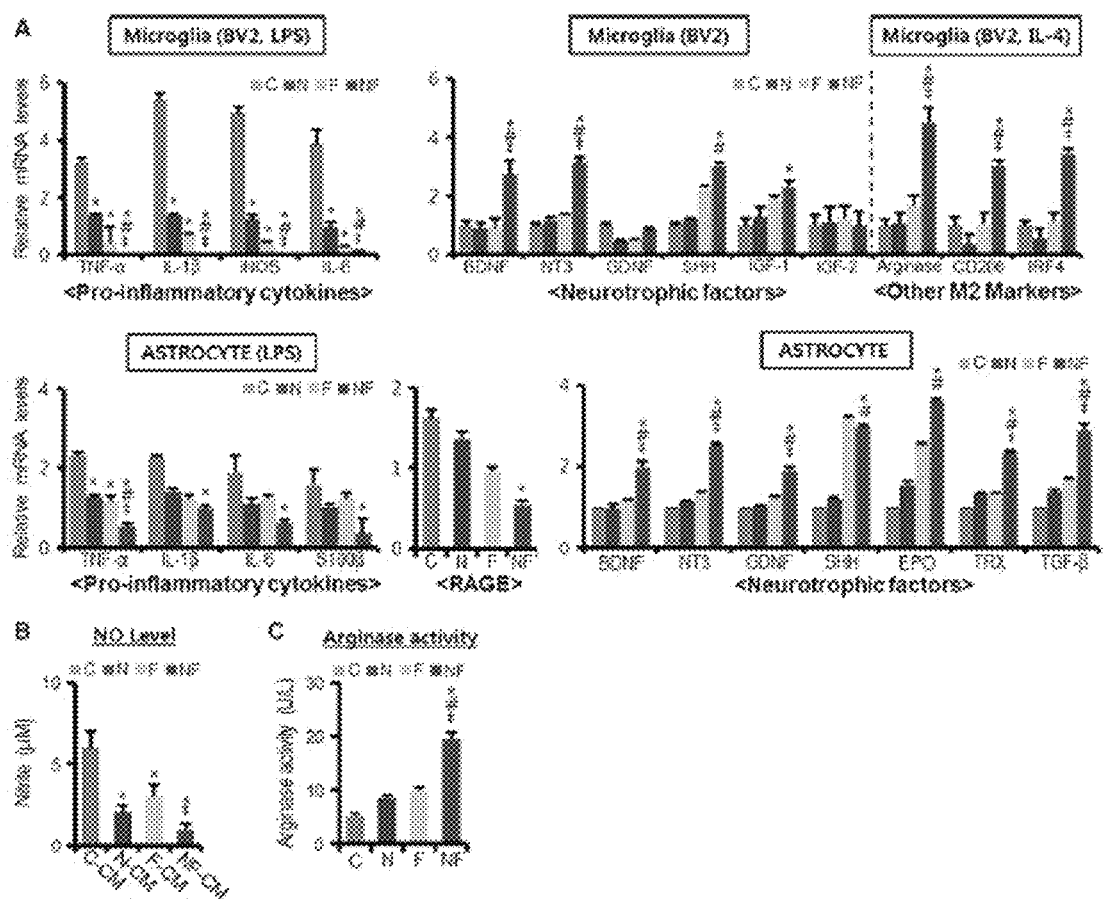
FIG. 5 shows mechanisms for paracrine neuroprotective roles by Nurr1- and Foxa2-expressing glial cells [A: Real-time PCR analysis showing a synergistic decrease in synthesis of inflammatory factors and a synergistic increase in synthesis of neurotrophic factors when Nurr1 and Fox2 are overexpressed in glial cells (microglia (upper panel) and astrocyte (lower panel)). BV2 microglial cells and primarily cultured astrocytes were transduced with C, N, F, and NF. Real-time PCR analyses were carried out 12 hours after LPS (100 ng/ml, for expression of pro-inflammatory cytokines), IL-4 (10 ng/ml, other M2 markers), or without treatment (neurotrophic factors). Significantly different from the control (C)*, N#, F‡ at P<0.05, n=3-6 PCRs; one-way ANOVA followed by a Bonferroni post hoc test. B: Graph illustrating a decrease in secretion of nitric oxide (NO) as an inflammatory factor in Nurr1+Foxa2-overexpressing microglial cells. C: Increase in activity of arginase as an enzyme that inhibits NO synthesis in Nurr1+Foxa2-overexpressing microglial cells. B and C: NO levels released (B) and arginase activity (C) were measured in media and cells for BV-2 microglial cell cultures, respectively. Significantly different from the control (C)*, N#, F‡ at P<0.05, n=3 reactions, P-values: 0.027 (N-CM*), 0.033 (F-CM*), 0.018 (NF-CM*), and 0.033 (NF-CM‡) for the NO level, 0.011*, 0.025#, and 0.036‡ for the arginase activity; one-way ANOVA followed by a Bonferroni post hoc test.

Next, the present inventors endeavored to identify the paracrine factors responsible for the Nurr1- and Foxa2-mediated neuroprotection. Saijo K et al, (2009) [A Nurr1/CoREST pathway in microglia and astrocytes protects dopaminergic neurons from inflammation-induced death. Cell 137: 47-59] has reported that the knockdown of Nurr1 aggravated the death of mDA neurons by increasing the production/release of pro-inflammatory cytokines from activated microglial cells. Consistent with this, the present inventors found that overexpression of Nurr1 in BV2 microglial cells led to a significant reduction in the expression of the pro-inflammatory cytokines, tumor necrosis factor-α (TNF-α), inducible nitric oxide (NO) synthase (iNOS), and interleukin-1β (IL-1β), upon exposure to the Toll-like receptor 4 (TLR4) ligand and lipopolysaccharide (LPS) (Upper panel of FIG. 5A). Interestingly, a decrease in pro-inflammatory cytokines expression was also evident in the Foxa2-expressing microglial cells, indicating that Foxa2 alone can exert an anti-inflammatory action without interacting with Nurr1. Importantly, the synergism of Nurr1 and Foxa2 was very dramatic, and transcripts of the pro-inflammatory cytokines were undetectable or barely detected after LPS treatment of the Nurr1+Foxa2-expressing BV2 cells (Upper panel of FIG. 5A). In line with the gene expression results, NO levels in the CM from the Nurr1+Foxa2-transduced microglial cells was lower than that in the CM from the control microglial cells (FIG. 5B). As well as the microglial cells, the astrocytes can create an inflammatory environment by releasing pro-inflammatory molecules, and similar patterns of pro-inflammatory cytokine expression decrease were seen in primary astrocytes transduced with Nurr1 and Foxa2 (Lower panel of FIG. 5A). S100β, a soluble protein released from astrocytes, acts as a damage-associated factor via receptor for advanced glycation end product (RAGE) pathways. The present inventors found that the Nurr1+Foxa2 expression in the astrocytes significantly decreased levels of S100β and RAGE (Lower panel of FIG. 5A).

Glial cells can be polarized into alternative phenotypes (an "alternative" M2 phenotype) versus a detrimental M1 phenotype resulting from macrophage activation (i.e., classical activation). The M2 phenotype can create a beneficial environment for neurons by secretion of neurotrophic factors such as neurotrophin 3 (NT3), a brain-derived neurotrophic factor (BDNF), a glial cell-derived neurotrophic factor (GDNF), erythropoietin, thioredoxin, transforming growth factor-β (TGF-β), sonic hedgehog (SHH) from astrocytes, and insulin-like growth factor 1/2 (IGF1/2) and BDNF from microglial cells. The observation of Nrf2 activation and expression of antioxidant genes in the mDA neurons after the Nurr1+Foxa2-CM treatment (FIGS. 4F and 4G) suggest that the Nurr1- and Foxa2-mediated paracrine actions involve the release of neurotrophic factors because these factors are major cytokines activating Nrf2 via the MAPK and PI3K pathways. Indeed, the primary astrocytes transduced with Nurr1 and/or Foxa2 expressed a significantly elevated levels of mRNAs for the trophic factors BDNF, NT3, GDNF, SHH, erythropoietin, thioredoxin, and TGF-β (Lower panel of FIG. 5A). The effect of the Nurr1+Foxa2 combination on the expression of BDNF, NT3, SHH, and IGF-1 was also evident in the BV2 microglial cells (Upper panel of FIG. 5A). The anti-inflammatory cytokines IL-4/IL-13 trigger M2 polarization of microglia by inducing arginase 1, CD206, and interferon regulatory factor 4 (IRF4). Upon the IL-4 treatment, the expression of M2 markers (FIG. 5A) as well as the arginase enzyme activity (FIG. 5C), was greatly increased in the Nurr1+Foxa2-transduced BV2 cells. These findings suggest that Nurr1 and Foxa2 in the glial cells additionally/synergistically exert neuroprotective effects on the mDA neurons via two paracrine pathways: (i) decreasing the production and release of pro-inflammatory cytokines (inflammatory factors) and (ii) enhancing the synthesis and secretion of neurotrophic factors.

Figure 8:
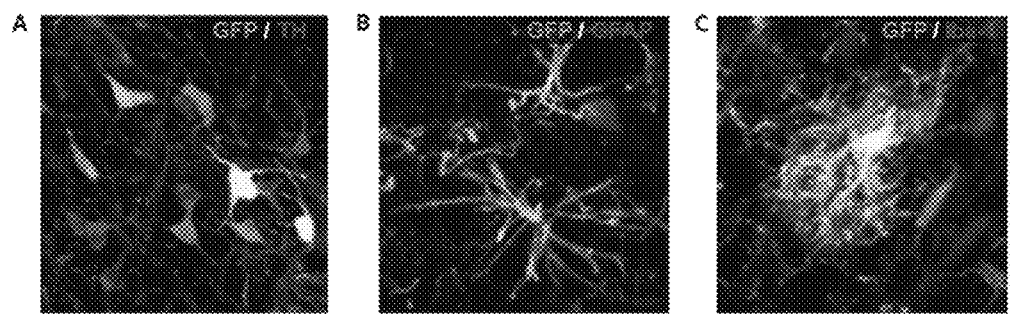
FIG. 8 shows that AAV genes used herein are easily transferred and expressed in dopaminergic neurons, astrocytes, and microglial cells.

Therapeutic Potential of AAV-Mediated Gene Delivery of Nurr1 and Foxa2 in Mouse Model of PD Based on the in vitro data by the present inventors, the present inventors examined whether the overexpression of Nurr1 and Foxa2 was able to forestall degeneration of the mDA neurons in PD. To this end, the present inventors chose the best-characterized MPTP mouse PD model (Beal M F (2001) Experimental models of Parkinson's disease. Nat Rev Neurosci 2: 325-334) using a subchronic systemic approach (intraperitoneal injection of 30 mg/kg of MPTP for five consecutive days) and an adeno-associated viral (AAV) system for gene delivery (schematically shown in FIGS. 6A and 6O). Because of the AAV's low immunogenicity, the lack of cytotoxic response, and the ability to infect non-dividing cells, clinical trials using it are currently under way in many disorders including PD. By injecting green fluorescent protein (GFP)-expressing AAVs into mouse midbrains, the present inventors confirmed the expression of transgenes in target cells expressing TH (DA neurons), GFAP (astrocytes), and Iba-1 (microglial cells) (FIG. 8).

Figure 6:
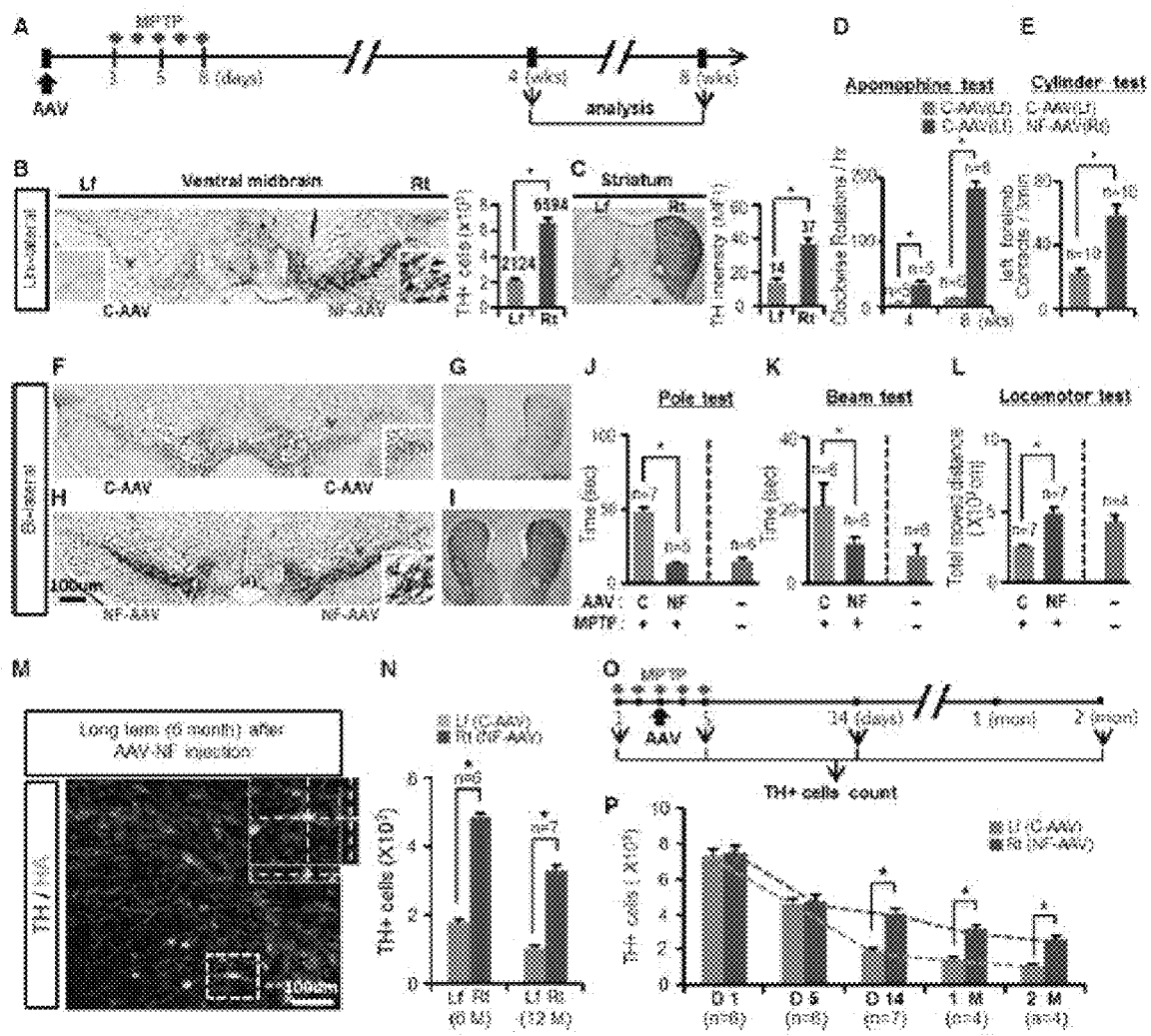
FIG. 6 shows therapeutic effects of AAV-mediated gene delivery of Nurr1+Foxa2 in a mouse PD model [A: Experimental scheme. PD model mice were generated by IP injection of MPTP, and AAVs expressing Nurr1 and Foxa2 (NF-AAV) or AAVs expressing an empty vector (Control, C-AAV) were stereotaxically injected 3 days prior to the initial MPTP treatment. B-E: Cytoprotective and behavioral effects of NF expression were assessed in PD mice unilaterally injected with NF-AAVs on the right side of midbrains. C-AAVs were injected into the left midbrains of the same mice. $TH^+$ mDA neurons numbers in the midbrain (B) and $TH^+$ fiber intensities in the striatum (C) of the NF-AAV injected to the right sides thereof were compared with those of the corresponding one injected to the left sides after 8 weeks. B: Data showing that most of dopaminergic neurons were destroyed in the midbrains (left) into which C-AAV is administered, whereas showing mDA neuroprotective effects by a MPTP toxin in the Nurr1+Foxa2-AAV-administered midbrains (right). Graph illustrates the number of viable mDA neuroprotective cells. Insets of (B), high-powered images of the areas indicated by red arrowheads in the C-AAV (left)- and NF-AAV (right)-injected sides. $TH^+$ cell numbers, *P=0.000078, n=7, a paired Student's t-test. The sectioned striatal tissues were immunofluorescently stained with TH, and $TH^+$ fiber intensities were evaluated from mean fluorescence intensities (MFI). n=56 microscopic fields at a magnification of 200× each for the left and right striatum. *P=0.000003; a paired Student's t-test. Behavioral asymmetry in the mice unilaterally injected with NF-AAVs (right side) was assessed using an apomorphine-induced rotation test (D) after 4 and 8 weeks. The cylinder test (E) was carried out after 8 weeks to determine left forelimbs movement. As the control, the behaviors were tested in PD mice bilaterally injected with C-AAV. *P=0.028 (rotation test), 0.043 (cylinder test); one-way ANOVA followed by a Bonferroni post hoc test. F to L: Behaviors of the PD mice injected with NF-AAVs bilaterally at both sides of the midbrain were assessed using the pole (J), beam (K) and locomotor (L) tests. *P=0.004 (pole), 0.044 (beam), and 0.045 (locomotor); one-way ANOVA followed by a Bonferroni post hoc test. Representative TH-stained midbrains (F and H) and left and right striatums (G and I) of the mice bilaterally injected with C-AAVs (F and G) and NF-AAVs (H and I) are shown (F to I). (F-I) show the representative TH-stained midbrains (F and H) and striatums (G and I) of the mice bidirectionally injected with C-AAVs (F and G) and NF-AAVs (H and I). M and N: Sustained mDA neuroprotective effects. A confocal image of TH/HA-stained cells 6 months after NF-AAV injection (Foxa2 gene tagged with HA) is shown in (M). Insets, z-stacked images of the boxed area along the y-axis (right panel) and x-axis (lower panel). $TH^+$ cells in the right (NF-AAV) and left (C-AAV injected) midbrains were counted 6 and 12 months after AAV injection (N). *P=0.000019 (6M), 0.000066 (12M), n=6-7; a paired Student's t-test. O and P: NF-AAV-mediated mDA neuroprotective effects were further assessed with the experimental schedule (0), in which AAV injections were subjected after three consecutive MPTP injections. $TH^+$ cells counted for the left and right sides of the midbrains are shown in (P). *P=0.000012 (D14), 0.000036 (1M), 0.000027 (2M), n=6-7; a paired Student's t-test].
Figure 7:
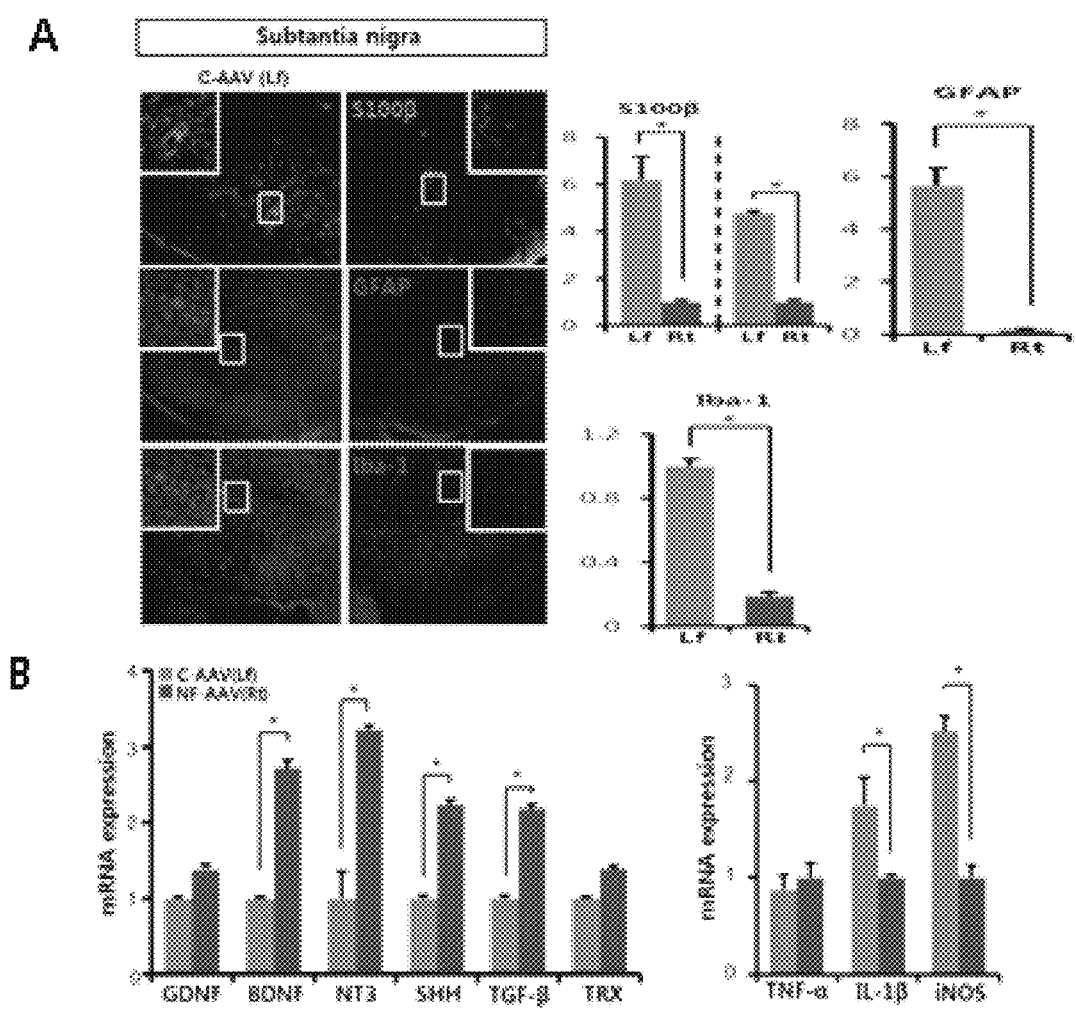
FIG. 7 shows a comparison of inflammation and pro-inflammatory/neurotrophic factor synthesis in the brains of the PD mice into which Nurr1 and Foxa2 are introduced and not introduced [A: Real-time PCR data showing a decrease in various inflammatory lesions (S100β, GFAP, and Iba-1) observed in the right midbrains of the PD mice to which Nurr1 and Foxa2-AAV are administered. B: Real-time PCR data showing increased synthesis of neurotrophic factors (left graph) and decreased synthesis of inflammatory factors (pro-inflammatory cytokines) in the midbrain tissue to which N+F-AAV is administered].
Figure 9:
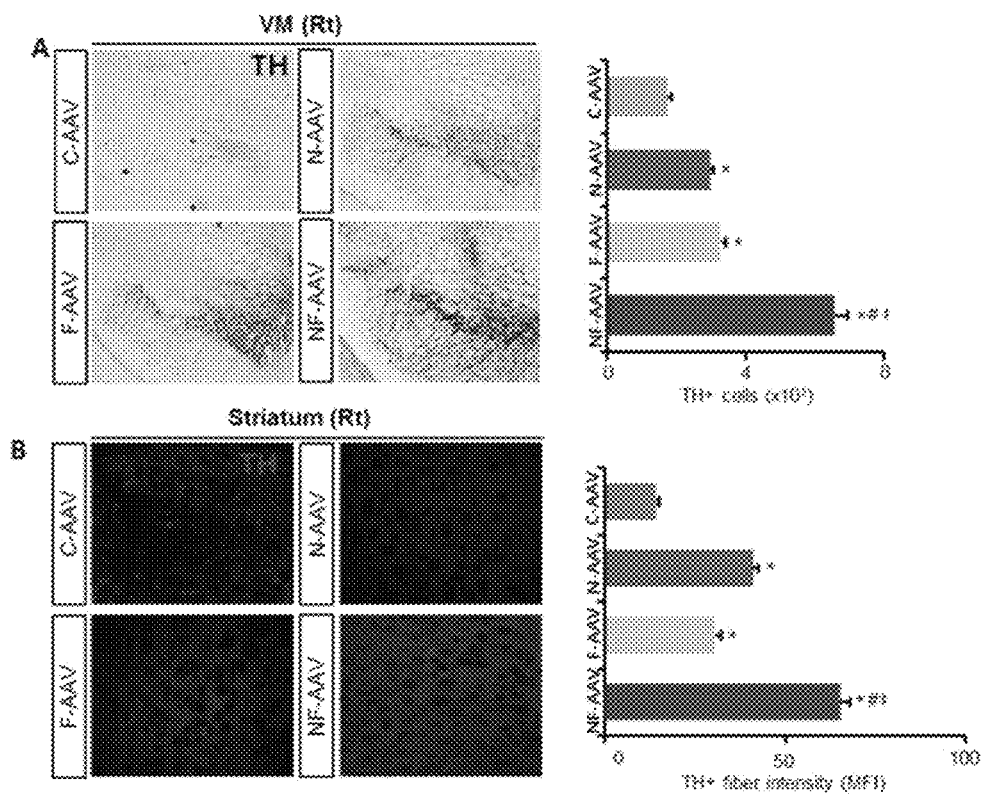
FIG. 9 demonstrates that combined Nurr1 and Foxa2-AAV injection is much more effective than single Nurr1-AAV or Foxa2-AAV injection to prevent loss of mDA neurons in SN and TH+ fiber intensity in striatum by intraperitoneally injecting the toxin MPTP.

Intraperitoneal injection of MPTP leadts to a gradual but massive loss of DA neurons in the midbrains: approximately 80-90% of the $TH^+$ mDA neurons have been lost 2 months after MPTP injection. DA neuronal losses on the two sides were not significantly difference. In this bilateral PD model, AAVs expressing Nurr1 and/or Foxa2 were injected into one side (right) of each midbrain (3 days prior to the MPTP treatment), whereas the other side (left) was injected with control-AAVs carrying an empty vector. The cytoprotective effect by injection of AAVs expressing the combination of Nurr1+Foxa2 was very dramatic, consistent, and reproducible. Without exception, $TH^+$ DA neuron numbers on the Nurr1+Foxa2-AAV-injected side were greater than those on the control side (at least >2.6-fold, n=7, P=0.000078, paired t-test) (FIGS. 6B and 9A). The average number of $TH^+$ DA neurons after 2 months was 6,594 cells on the Nurr1+Foxa2-AAV-injected side versus 2,124 cells on the control side. Based on the average $TH^+$ cell number counted in MPTP-untreated midbrains (8,143 cells), our TH+ cell counts indicate that 69% of the mDA neurons were rescued from MPTP-induced degeneration by Nurr1+Foxa2-AAV. Injection of Nurr1-AAV or Foxa2-AAV alone had much less effect than the combined treatment (FIG. 9). In accord with the in vitro findings shown in FIG. 5A, the transcript and protein levels of cytotoxic mediators S100β and GFAP were greatly reduced on the Nurr1+Foxa2-AAV-injected sides of the midbrain (FIG. 7A). Also, the mRNA levels of the pro-inflammatory cytokines IL-1b and iNOS were significantly lower in the Nurr1+Foxa2-AAV-injected side than those of the control sides, while the expressions of BDNF, NT3, SHH, and TGF-β were greater in the Nurr1+Foxa2-AAV-injected sides (FIG. 7B). Nigrostriatal DAergic innervation was also substantially protected on the Nurr1+Foxa2-AAV-injected side, as shown by the TH+ fibers intensities in the striatum (mean fluorescent intensity (MFI): 37 on the Nurr1+Foxa2-AAV-injected versus 14 on the control side) (FIG. 6C). Consequently, the mice displayed massive rotator behaviors toward the Nurr1+Foxa2-AAV-injected side (right, clockwise) when the DA receptor agonist apomorphine was intraperitoneally injected (FIG. 6D). Furthermore, when locomotor activity was estimated by the cylinder test 8 weeks after the MPTP treatment, the mice injected with Nurr1+Foxa2-AAV on the right side (a control-AAV group injected on the left side) more often used their left forelimbs, when rearing against a wall than did the mice injected with control-AAV on both sides (FIG. 6E), while the numbers of right forelimbs contacts were not significantly different between the groups (46.5±6.9 vs. 50.1±5.7/3 min).

The present inventors addressed several practical issues in PD therapy. First, the present inventors examined the effects of bilateral Nurr1+Foxa2-AAV (the left and right sides) injection on behaviors of the MPTP-treated mice, since both sides of the SN are commonly affected in PD patients. Along with its strong protective effects on mDA neurons and striatal DA fiber innervation (FIGS. 6F-6I) bilateral Nurr1+Foxa2-AAV injection substantially protected the behaviors assessed by a pole test (FIG. 6J), a beam test (FIG. 6K), and a locomotor test (FIG. 6L). Another issue is maintenance of the therapeutic effect. AAV-delivered transgene expression was sustained for up to 6 months (FIG. 6M), and the Nurr1+Foxa2-mediated cytoprotective effects were evident 1 year after the gene delivery (FIG. 6N). In most cases, the treatment starts in PD patients undergoing progressive degenerative process. Therefore, the present inventors examined the effect of Nurr1+Foxa2-AAV on the midbrains already undergoing degeneration. To do this, Nurr1+Foxa2-AAVs were injected 2 days after the initial injection of MPTP (FIG. 6O). Around 40% of the mDA neurons in the midbrains were lost for 1 to 5 days after the MPTP treatment, and TH+ cell numbers on the right side (an Nurr1+Foxa2-AAV-injected group) were not different from those on the left side (a C-AAV-injected group) on the day 5 after the MPTP treatment (FIG. 6P, probably because expression of the exogenous Nurr1 and Foxa2 from the AAVs takes several days. DA neuron numbers on the left side declined greatly by days 5-14 (from 4,629 cells on the day 5 to 1,904 cells on the day 14; 2,725 mDA neurons lost). By contrast, 4,056 TH+ mDA neurons on the Nurr1+Foxa2-AAV-injected right side of the midbrain survived on the day 14, resulting in the loss of only 682 mDA neurons on days 5-14. The Nurr1+Foxa2-mediated neuroprotective effect was further detected up to 2 months (FIG. 6P). Based on these findings, the present inventors propose that the AAV-mediated Nurr1+Foxa2 gene delivery is a promising therapeutic tool in inflammatory neurologic disorders.

Neurotropic/Inflammatory Gene Expressions in the Host Brain Grafted with Cultured Astrocytes.

Figure 11:
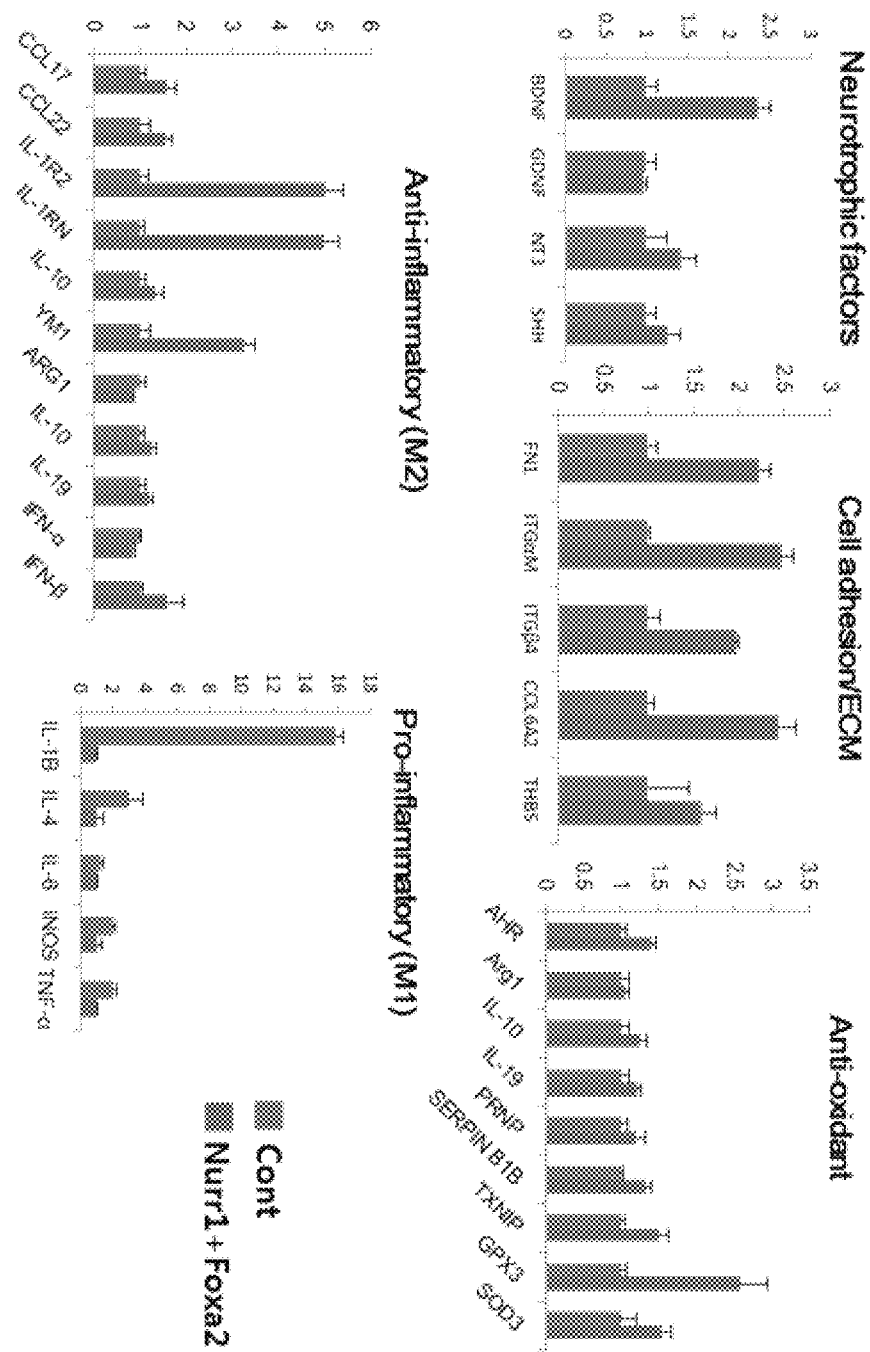
FIG. 11 shows that neurotropic/inflammatory gene expressions in the host brain grafted with cultured astrocytes. 6OHDA-lesioned PD rats were received transplantation with NF-VM-astrocytes or control VM-astrocytes. One month after transplantation, the graft-host interfaces were dissected as described in examples. Real-time-qPCRs were carried out for the gene expressions associated with neurotrophic/hostile brain environments.

Upregulated expression pattern of neurotrophic, antioxidant, and ECM genes was shown in the brains grafted with N+F-transduced VM-astrocytes than those transplanted with control VM-astrocytes. M1-to-M2 polarization by N+F-VM-astrocyte transplantation was further clarified in the gene expression analysis exhibiting downregulated pro-inflammatory/M1 and upregulated anti-inflammatory/M2 phenotype gene expressions in the brains transplanted with N+F-VM-astrocytes than those grafted with control VM-astrocytes. These findings together indicate that transplantation of cultured VM-astrocytes could establish a neurotrophic brain environment, and that Nurr1+Foxa2 expression in the donor astrocytes further additionally contribute to establishing a neurotrophic/neuroprotective brain milieu (FIG. 11).

CONCLUSION

Current symptomatic treatment of PD cannot halt disease progression. To overcome this limitation, disease-modifying strategies are being sought. Discouraging results have been obtained in clinical trials of neurotrophic factors in the treatment of neurologic disorders. While there are many possible reasons for these failures, there is a consensus that the delivery of cytokines and chemicals to their desired neuronal targets within the central nervous system (CNS) is a challenge. Even local administration of trophic factors directly to the vicinity of the desired site appeared to give discouraging outcomes due to inefficient diffusion to the target site. Furthermore, adverse side effects can be expected from the systemic administration and/or broad-spectrum action of candidate drugs. These difficulties prompt an alternative approach involving manipulating factors associated with neurotrophic or cytoprotective processes in mDA neurons at the gene levels, for example, by exploiting transduction by viral vectors.

In the present invention, the present inventors examined the combined expression of Nurr1 and Foxa2 as a therapeutic tool for PD that is a representative example of the inflammatory neurologic disorder. The rationale for this was as follows. First, both factors are expressed in the mDA neurons of the adult SN and interact to promote the survival of these neurons and protect them against toxic insults. However, the levels of these factors decrease during aging and degeneration. Overexpression of the genes, which are associated with target functions in normal physiology, but lost in a pathologic state, would be an appropriate option for the therapeutic development. Genome-wide profiling studies have demonstrated that PD pathology is associated with broad transcriptional dysregulation (Cooper-Knock J, Kirby J, Ferraiuolo L, Heath P R, Rattray M, Shaw P J (2012) Gene expression profiling in human neurodegenerative disease. Nat Rev Neurol 8: 518-530 Cooper-Knock et al., 2012). Thus, the decreased Nurr1 and Foxa2 levels observed could be interpreted as part of the context of PD pathology. α-Synuclein, the clumps of which are hallmarks of PD, has been suggested as an important cause of the perturbation of gene transcription in PD. In particular, the accumulation of α-synuclein is associated with the downregulation of the transcription factors critical for neuronal survival, including Nurr1, myocyte enhancer factor-2D, DNA methyltransferase 1, and a transcription factor EB. In addition, other factors related to oxidative stress and inflammatory reactions may directly or indirectly influence on levels of proteins via protein degradation.

Second, the strategies proposed in the present invention would be less hazardous as it is without tumorigenic side effects. Gene therapy with molecules involved in survival pathways, for example, Akt-mTOR, has been suggested for PD. However, most of these signaling molecules are involved in a broad spectrum of cellular events, including the cell cycles. By contract, Nurr1 and Foxa2 are rather specific for the development, maintenance, and survival of mDA neurons in the midbrains, and their tumorigenic potentials are expected to be quite low, given the strong cell cycle arrest induced by their overexpression.

Third, in addition to the protective roles of Nurr1 and Foxa2 in the mDA neurons, the overexpression of Nurr1 and Foxa2 in the glial cells shifts a diseased environment surrounding mDA neurons in the midbrain toward a therapeutic one by reducing a level of pro-inflammatory cytokines as well as by increasing the releases of neurotrophic cytokines.

Figure 10:
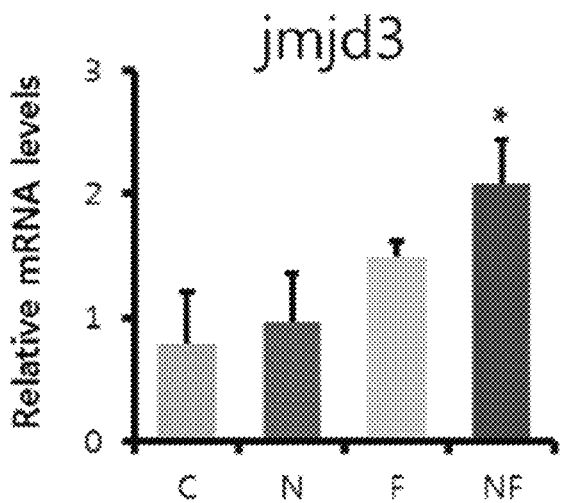
FIG. 10 shows that expression of Jumonji significantly increases when Nurr1 and Foxa2 are co-expressed in microglial cells.

Because of this, the combined expression of Nurr1+Foxa2 could become an ideal and prospective therapeutic approach, and one superior to strategies involving exclusively intrinsic or extrinsic modes of action. Epigenetic regulation by Nurr1 and Foxa2 may possibly involve the regulation of expression of the pro-inflammatory/trophic factors. In addition to the trans-repressive (a tendency of one protein toward inhibiting the activity of another protein due to the interaction between the proteins) role of Nurr1 (Saijo K et al, (2009) A Nurr1/CoREST pathway in microglia and astrocytes protects dopaminergic neurons from inflammation-induced death. Cell 137: 47-59), the present inventors have shown that Nurr1 and Foxa2 activate gene transcription epigenetically by opening chromatin structures by histone acetylation and methylation. Consistant with this, histone deacetylase (HDAC) inhibitors increase neurotrophic factor release from glial cells. Furthermore, the H3K27me3 histone demethylase, Jumonji domain 3 (jmjd3), is essential for polarization of microglial cells toward an M2 phenotype expressing the neurotrophic factors, and jmjd3 mRNA in BV2 microglial cells was up-regulated by the combined expression of Nurr1 and Foxa2 (FIG. 10).

AAVs are very poorly immunogenic and thus persist for years as extrachromosomal episomes. AAVs (serotype 2) have been predominantly used in current gene therapeutic trials, because of their proven efficacy and safety. Thus with clinical trial in mind, the present inventors used the AAV vector system for the delivery of Nurr1 and Foxa2 genes into the PD mouse SN. The present inventors showed that the expression of the AAV-mediated transgene was efficiently induced in the midbrain SN over a prolonged period (at least 6 months) and that the combined expression of the Nurr1+Foxa2 transgene strongly protected the mDA neurons from MPTP neurotoxin and restored behaviors associated with nigrostriatal DA neurotransmission. The neuroprotective effect of the delivery of Nurr1+Foxa2-AAV genes was not only dramatic (ca 70% of the mDA neurons were protected from MPTP-induced neurodegeneration) but also completely reproducible: Numbers of surviving $TH^+$ DA neurons in the SN injected with Nurr1+Foxa2-AAV were always far greater than in the control SN. AAV-induced transgene expression was detected in all types of cells in the midbrain-neurons, astrocytes, and microglial cells-in the specific experimental conditions of the present invention.

The present invention is directed to a therapeutic effect of Nurr1 and Foxa2 in inflammatory neurologic disorders by M1-to-M2 polarization of glial cells and thus can be used for gene therapy of all types of neurologic disorders which are accompanied with inflammation and cause destruction of neurons.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A method of protecting brain neurons from cell damage comprising:

administering to a mammal a recombinant viral vector comprising a nucleic acid expressing Nuclear receptor-related factor 1 (Nurr1) and forkhead box protein A2 (Foxa2) to transduce glial cells that are adjacent to neurons to form transduced glial cells; and expressing Nurr1 and Foxa2 proteins from the recombinant viral vector, wherein expression of both Nurr1 and Foxa2 proteins in the transduced glial cells reduces secretion of one or more inflammatory factors and increases secretion of one or more neurotrophic factors that protect the neurons from cell damage relative to transduced glial cells expressing Nurr1 or Foxa2 alone.

2. The method of claim 1, wherein the glial cells are astrocytes or microglial cells.

3. The method of claim 1, wherein the viral vector is an adeno-associated viral (AAV) or lentiviral vector.

4. The method of claim 1, wherein the glial cells are transduced in vivo into a mammalian brain by administering the recombinant viral vector into a mammal by injection.

5. The method of claim 4, wherein transduction of the glial cells results in reduced secretion levels of one or more inflammatory factors selected from the group consisting of: S100β and glial fibrillary acidic protein (GFAP).

6. The method of claim 4, wherein transduction of the glial cells results in increased secretion levels of one or more protective neurotrophic factors selected from the group consisting of: brain-derived neurotrophic factor (BDNF), neurotrophin 3 (NT3), sonic hedgehog (SHH) and Transforming Growth Factor-β (TGF-β).

7. The method of claim 1, wherein transducing the glial cells with the recombinant viral vector comprises transducing the glial cells with a recombinant viral vector comprising an expression control sequence operably linked to the Nurr1 and Foxa2 nucleic acids.

8. A method of protecting brain neurons from cell damage in a mammalian subject in need thereof, comprising:
   injecting into the subject a recombinant viral vector comprising a nucleic acid expressing Nuclear receptor-related factor 1 (Nurr1) and forkhead box protein A2 (Foxa2) to target and transduce brain glial cells; and
   expressing Nurr1 and Foxa2 proteins from the recombinant viral vector, wherein expression of both Nurr1 and Foxa2 proteins in the transduced brain glial cells reduces secretion of one or more inflammatory factors and increases secretion of one or more neurotrophic factors that protect neurons from cell damage relative to transduced brain glial cells expressing Nurr1 or Foxa2 alone.

9. The method of claim 8, wherein the glial cells are astrocytes or microglial cells.

10. The method of claim 8, wherein transduction of the brain glial cells results in reduced levels of inflammatory factors selected from the group consisting of: S100β and glial fibrillary acidic protein (GFAP).

11. The method of claim 8, wherein transduction of the brain glial cells results in increased levels of one or more protective neurotrophic factors selected from the group consisting of: brain-derived neurotrophic factor (BDNF), neurotrophin 3 (NT3), sonic hedgehog (SHH) and Transforming Growth Factor-β (TGF-β).

12. The method of claim 8, wherein the recombinant viral vector is an adeno-associated viral (AAV) vector or lentiviral vector.

13. The method of claim 8, wherein injecting into the mammalian subject comprises injecting into the brain of the mammalian subject.

* * * * *

SEQUENCE LISTING

```
<160> NUMBER OF SEQ ID NOS: 42

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
cgtcagccga tttgctatct                                              20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
cggactccgc aaagtctaag                                              20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
gcccatcctc tgtgactcat                                              20

<210> SEQ ID NO 4
<211> LENGTH: 20
<212> TYPE: DNA
<213> ORGANISM: Artificial Sequence
```

```
<220> FEATURE:
<223> OTHER INFORMATION: primer

<400> SEQUENCE: 4
aggccacagg tattttgtcg                                               20

<210> SEQ ID NO 5
<211> LENGTH: 22
<212> TYPE: DNA
<213> ORGANISM: Artificial Sequence
<220> FEATURE:
<223> OTHER INFORMATION: primer

<400> SEQUENCE: 5
cctcctttgc ctctcactct tc                                            22

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
agtattagag cggtggcatg gt                                            22

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
atggatgcta ccaaactgga t                                             21

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
tgaaggactc tggctttgtc t                                             21

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
gtgacagtat tagcgagtgg g                                             21

<210> SEQ ID NO 10
<211> LENGTH: 17
<212> TYPE: DNA
<213> ORGANISM: Artificial Sequence
<220> FEATURE:
<223> OTHER INFORMATION: primer

<400> SEQUENCE: 10
gggtagttcg gcattgc                                                  17
```

```
<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
ggtcagaatt ccagccgatg a                                              21

<210> SEQ ID NO 12
<211> LENGTH: 21
<212> TYPE: DNA
<213> ORGANISM: Artificial Sequence
<220> FEATURE:
<223> OTHER INFORMATION: primer

<400> SEQUENCE: 12
ggcacacaca caggaagtgt c                                              21

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
cgcccgccga agaccactcc                                                20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
gtcgaaggcg accggcctgc                                                20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
aaaagctgac ccctttagcc                                                20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
tgcacctctg agtcatcagc                                                20

<210> SEQ ID NO 17
<211> LENGTH: 18
<212> TYPE: DNA
<213> ORGANISM: Artificial Sequence
<220> FEATURE:
<223> OTHER INFORMATION: primer
```

```
<400> SEQUENCE: 17
tgctcttcag ttcgtgtg                                                    18

<210> SEQ ID NO 18
<211> LENGTH: 19
<212> TYPE: DNA
<213> ORGANISM: Artificial Sequence
<220> FEATURE:
<223> OTHER INFORMATION: primer

<400> SEQUENCE: 18
acatctccag tctcctcag                                                   19

<210> SEQ ID NO 19
<211> LENGTH: 24
<212> TYPE: DNA
<213> ORGANISM: Artificial Sequence
<220> FEATURE:
<223> OTHER INFORMATION: primer

<400> SEQUENCE: 19
acaacttcga tttgaaccac attc                                             24

<210> SEQ ID NO 20
<211> LENGTH: 22
<212> TYPE: DNA
<213> ORGANISM: Artificial Sequence
<220> FEATURE:
<223> OTHER INFORMATION: primer

<400> SEQUENCE: 20
gagagctcaa accatgcaaa ct                                               22

<210> SEQ ID NO 21
<211> LENGTH: 21
<212> TYPE: DNA
<213> ORGANISM: Artificial Sequence
<220> FEATURE:
<223> OTHER INFORMATION: primer

<400> SEQUENCE: 21
gaggcagaaa atgtcacgat g                                                21

<210> SEQ ID NO 22
<211> LENGTH: 21
<212> TYPE: DNA
<213> ORGANISM: Artificial Sequence
<220> FEATURE:
<223> OTHER INFORMATION: primer

<400> SEQUENCE: 22
cttccacctc cattcttttc c                                                21

<210> SEQ ID NO 23
<211> LENGTH: 27
<212> TYPE: DNA
<213> ORGANISM: Artificial Sequence
<220> FEATURE:
<223> OTHER INFORMATION: primer

<400> SEQUENCE: 23
cgtggtggac ttctctgcta cgtggtg                                          27
```

<210> SEQ ID NO 24
<211> LENGTH: 27
<212> TYPE: DNA
<213> ORGANISM: Artificial Sequence
<220> FEATURE:
<223> OTHER INFORMATION: primer

<400> SEQUENCE: 24
ggtcggcatg catttgactt cacagtc                                27

<210> SEQ ID NO 25
<211> LENGTH: 19
<212> TYPE: DNA
<213> ORGANISM: Artificial Sequence
<220> FEATURE:
<223> OTHER INFORMATION: primer

<400> SEQUENCE: 25
caccggagag ccctggata                                         19

<210> SEQ ID NO 26
<211> LENGTH: 19
<212> TYPE: DNA
<213> ORGANISM: Artificial Sequence
<220> FEATURE:
<223> OTHER INFORMATION: primer

<400> SEQUENCE: 26
tgtacagctg ccgcacaca                                         19

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
gcagctcact ttggatgaca                                        20

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
ccaaacgtca caggacattg                                        20

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
gtgaagaacc cacggtctgt                                        20

<210> SEQ ID NO 30
<211> LENGTH: 20
<212> TYPE: DNA
<213> ORGANISM: Artificial Sequence
<220> FEATURE:
<223> OTHER INFORMATION: primer

```
<400> SEQUENCE: 30
ctggttgtca ggggagtgtt                                        20

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
atgccacgtg ggaaaatctg                                        20

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
tgtagcagtg gcctgcatag                                        20

<210> SEQ ID NO 33
<211> LENGTH: 21
<212> TYPE: DNA
<213> ORGANISM: Artificial Sequence
<220> FEATURE:
<223> OTHER INFORMATION: primer

<400> SEQUENCE: 33
ggcggcaaaa ggtgaccagg a                                      21

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
gccctcatgt ctgccacggg                                        20

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
cagcatcagg gtcacagaaa                                        20

<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
ctggttggag aaggaagtgc                                        20
```

```
<210> SEQ ID NO 37
<211> LENGTH: 21
<212> TYPE: DNA
<213> ORGANISM: Artificial Sequence
<220> FEATURE:
<223> OTHER INFORMATION: primer

<400> SEQUENCE: 37
gcagacctca cagacgttgc t                                              21

<210> SEQ ID NO 38
<211> LENGTH: 21
<212> TYPE: DNA
<213> ORGANISM: Artificial Sequence
<220> FEATURE:
<223> OTHER INFORMATION: primer

<400> SEQUENCE: 38
aggctggttt ctcggatctg g                                              21

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
agtccattgt gcccatgatt                                                20

<210> SEQ ID NO 40
<211> LENGTH: 20
<212> TYPE: DNA
<213> ORGANISM: Artificial Sequence
<220> FEATURE:
<223> OTHER INFORMATION: primer

<400> SEQUENCE: 40
gcagtagtag gcaggctcgt                                                20

<210> SEQ ID NO 41
<211> LENGTH: 21
<212> TYPE: DNA
<213> ORGANISM: Artificial Sequence
<220> FEATURE:
<223> OTHER INFORMATION: primer

<400> SEQUENCE: 41
gctcctcctg ttcgacagtc a                                              21

<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42
accttcccca tggtgtctga                                                20
```